(12) United States Patent
Rubino et al.

(10) Patent No.: US 9,890,325 B2
(45) Date of Patent: Feb. 13, 2018

(54) METHOD FOR LABELING NANOCLAY FOR TRACKING THEM WITHIN DIFFERENT SOLID AND LIQUID MATERIAL

(71) Applicant: Board of Trustees of Michigan State University, East Lansing, MI (US)

(72) Inventors: Maria I. Rubino, East Lansing, MI (US); Rafael A. Auras, Okemos, MI (US); Krishnamurthy Jayaraman, East Lansing, MI (US); Yining Xia, Lansing, MI (US); Carlos Diaz, West Henrietta, NY (US); Joe Hotchkiss, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 20 days.

(21) Appl. No.: 15/230,128

(22) Filed: Aug. 5, 2016

(65) Prior Publication Data
US 2016/0340576 A1 Nov. 24, 2016

Related U.S. Application Data

(62) Division of application No. 14/069,556, filed on Nov. 1, 2013, now Pat. No. 9,435,737.

(60) Provisional application No. 61/721,185, filed on Nov. 1, 2012.

(51) Int. Cl.
| | |
|---|---|
| G01N 33/00 | (2006.01) |
| C09K 11/02 | (2006.01) |
| G01N 21/64 | (2006.01) |
| C09K 11/06 | (2006.01) |
| B29C 47/00 | (2006.01) |
| B29K 23/00 | (2006.01) |
| B29K 105/16 | (2006.01) |
| B29K 509/00 | (2006.01) |

(52) U.S. Cl.
CPC ............ *C09K 11/025* (2013.01); *C09K 11/06* (2013.01); *G01N 21/643* (2013.01); *B29C 47/0004* (2013.01); *B29K 2023/12* (2013.01); *B29K 2105/162* (2013.01); *B29K 2509/00* (2013.01); *B29K 2995/0035* (2013.01); *C09K 2211/1088* (2013.01)

(58) Field of Classification Search
None
See application file for complete search history.

(56) References Cited

PUBLICATIONS

Johnston, A.P.R. et al., A Mechanism for Forming Large Fluorescent Organo-Silica Particles; Potential Supports for Combinatorial Synthesis, 2006, Checm. Mater. vol. 18, pp. 6163-6169.

(Continued)

*Primary Examiner* — Robert Xu
(74) *Attorney, Agent, or Firm* — Howard & Howard Attorneys PLLC

(57) ABSTRACT

A method of monitoring a location of a nanoparticle within a material is described herein. The method includes the steps of providing at least one nanoclay particle, attaching a fluorescent tag to the at least one nanoclay particle, and determining a fluorescence of the fluorescent-labeled nanoclay particle. The method also includes forming the material including the at least one fluorescent-labeled nanoclay particle, depositing the material in an aqueous solution, and detecting a movement of the fluorescent-labeled nanoclay particle from the material to the aqueous solution.

14 Claims, 16 Drawing Sheets

(56) References Cited

PUBLICATIONS

Ribeiro, T. et al., Synthesis and Characterization of Perylenediimide Labeled Core-Shell Hybrid Silica-Polymer Nanoparticles, 2009, Journal of Physical Chemistry C vol. 113(42), pp. 18082-18090.

Saleh, S.M. et al., Novel multicolor fluorescently labeled silica nanoparticles for interface fluorescence resonance energy transfer to and from labeled avidin, 2010, Analytical Bioanalytical Chemistry, vol. 398, pp. 1615-1623.

Panzera, A., Novel blood platelet diagnostic platform, 2011, A thesis for the degree of Master of Science, Dublin City University.

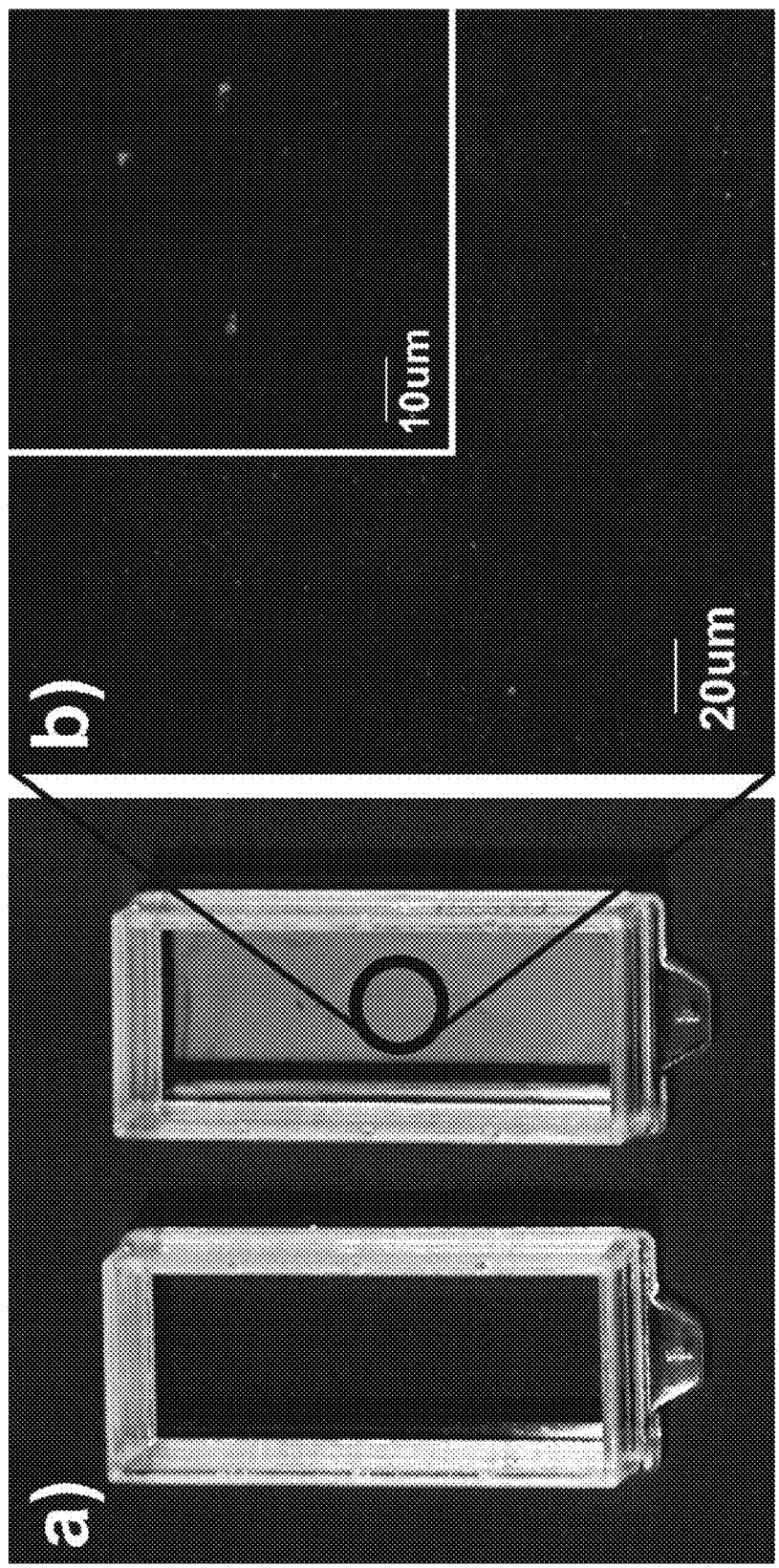

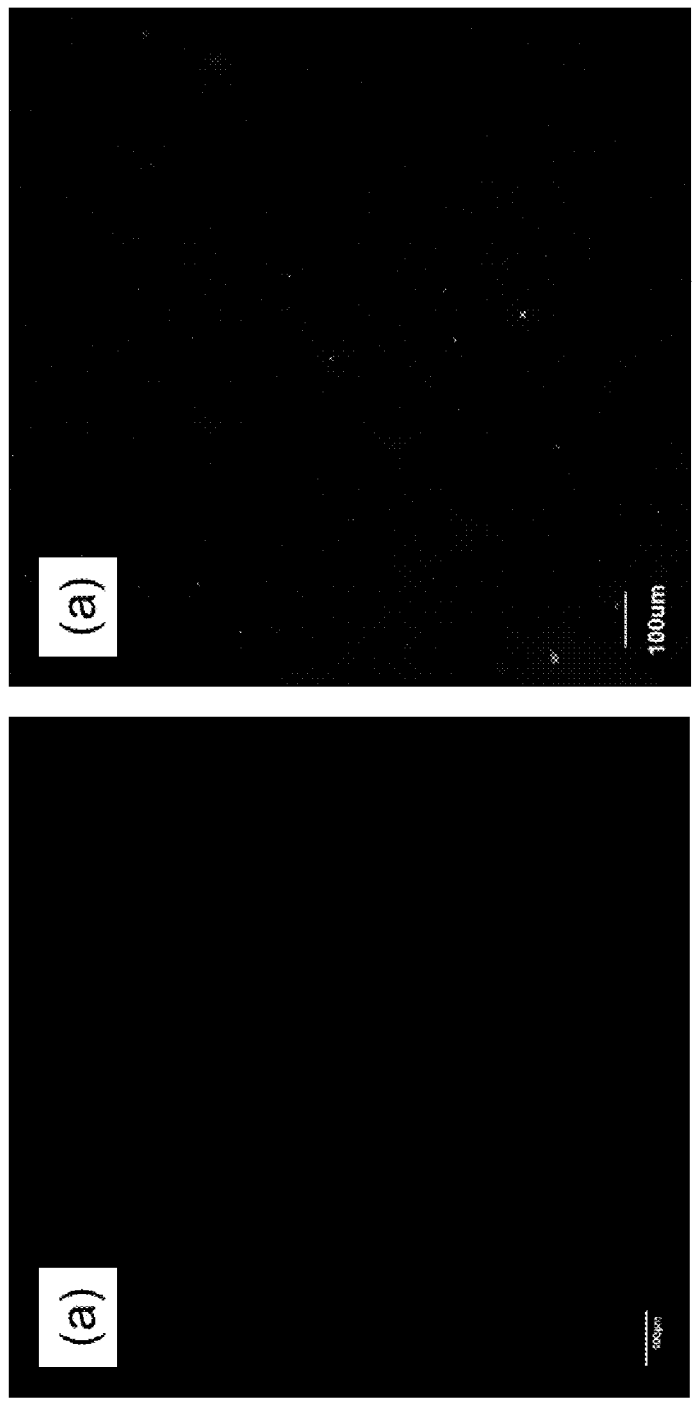

METHOD FOR LABELING NANOCLAY FOR TRACKING THEM WITHIN DIFFERENT SOLID AND LIQUID MATERIAL

CROSS REFERENCE TO RELATED APPLICATION

This application is a divisional of U.S. patent application Ser. No. 14/069,556, filed Nov. 1, 2013, which claims priority to U.S. Provisional Patent Application Ser. No. 61/721,185, filed Nov. 1, 2012, the disclosures of which are hereby incorporated by reference in their entirety.

TECHNICAL FIELD

The subject matter disclosed herein relates generally to engineered nanomaterials (ENMs) and, more particularly, to a fluorescent-labeled nanoclay particle and methods of monitoring a position of a nanoclay within materials such as nanocomposite polymers or biological systems.

BACKGROUND OF THE INVENTION

Engineered nanomaterial (ENM) production has expanded significantly in the last decade, with sales increased from $0.4 billion (USD) in 2005 to $1.4 billion (USD) in 2010. See Frost & Sullivan, *Nanomaterials—Strategic Portfolio Management* (Technical Insights), 2010. Sales of nanocomposites, produced by the addition of ENMs to polymeric matrices, are estimated to reach $2.4 billion (USD) by 2016. See BCC Research NAN021E—*Global Markets for Nanocomposites, Nanoparticles, Nanoclays, and Nanotubes*. As applications for ENMs continue to expand, there is increasing concern about potential health and environmental risks associated with exposure to nanoparticles from ENMs. The nanoparticles, due to their small size, high surface area and surface reactivity, have the potential to induce cytotoxic effects, see for example, Magrez, A.; Kasas, S.; Salicio, V.; Pasquier, N.; Seo, J. W.; Celio, M.; Catsicas, S.; Schwaller, B.; Forró, L. *Nano Lett.* 2006, 6, 1121, as well as genotoxic effects, inflammation and even cancer. See for example, Magrez, A.; Kasas, S.; Salicio, V.; Pasquier, N.; Seo, J. W.; Celio, M.; Catsicas, S.; Schwaller, B.; Forró, L. *Nano Lett.* 2006, 6, 1121 and Savolainen, K.; Alenius, H.; Norppa, H.; Pylkkänen, L.; Tuomi, T.; Kasper, G. *Toxicol.* 2010, 269, 92.

Currently, there is a lack of information to quantify exposure to ENMs and the associated concerns. The basic transport and fate of nanoparticles from nanocomposites when exposed to different conditions are not well understood nor are their effects on biological systems and the environment. A research strategy report recently issued by the National Research Council in the U.S. stresses the need to assess the risk associated with exposure to ENMs, including modeling the fate and transport of nanoparticles. See for example, NRC (National Research Council) A Research Strategy for Environmental, Health, and Safety Aspects of Engineered Nanomaterials; *National Academy Press*: Wash., D.C., 2012, EFSA (European Food Safety Authority) EFSA Journal 2009, 958, 1-39, and Johnston, J. M.; Lowry, M.; Beaulieu, S.; Bowles, E. State-of-the-Science Report on Predictive Models and Modeling Approaches for Characterizing and Evaluating Exposure to Nanomaterials. U.S. Environmental Protection Agency: Washington, D.C., 2010. EPA/600/R-10/129 (NTIS PB2011-105273).

Nanoclays, such as organically modified montmorillonite (o-MMT), are most widely used for nanocomposite applications in the packaging and automotive parts industries because of their natural abundance, high mechanical strength, and high aspect ratio. See for example, Marquis, D. M.; Guillaume, E.; Chivas-Joly, C. In Nanocomposites and Polymers with Analytical Methods; 2005; pp. 261-284 and Jiang, T.; Wang, Y.; Yeh, J.; Fan, Z. *Eur Polym J* 2005, 41, 459-466. The good efficiency-cost balance of o-MMT as a nanofiller accounts for its use in about half of the entire nanocomposite market (approximately 60,000 metric tons in 2011). When o-MMT is compounded with polymers and exposed to moderate temperatures, these nanoparticles can move within the polymer matrix towards the surface and migrate to the surroundings. Non-diffusive mechanisms for nanoclay particle migration have been proposed to explain increases in the o-MMT content of nanocomposite surfaces during heating of polypropylene (PP)/o-MMT and nylon-6/o-MMT. See for example, Lewin, M. *Fire Mater* 2003, 27, 1-7, Zammarano, M.; Gilman, J. W.; Nyden, M.; Pearce, E. M.; Lewin, M. *Macromol Rapid Comm* 2006, 27, 693-696, Tang, Y.; Lewin, M.; Pearce, E. M. *Macromol Rapid Comm* 2006, 27, 1545-1549, Tang, Y.; Lewin, M. *Polym Degrad Stabil* 2007, 92, 53-60, and Lewin, M.; Tang, Y. *Macromolecules* 2008, 13-17. The movement of nanoclay particles could also be modified by other factors such as interaction with different solvents and radiation. A better understanding of migration in nanocomposites is extremely important for determining exposure dose, and this requires knowledge of the basic mass transport parameters of the nanoparticles.

Challenges in evaluating the transport and fate of ENMs from nanocomposites include the lack of tools and methodologies available to adequately track their movement and position. See for example, EFSA (European Food Safety Authority) EFSA Journal 2011, 9, 2140. The current approaches for tracking and detecting nanoclays involve elemental analysis via atomic absorption spectrometry (AAS) or inductively coupled plasma mass spectroscopy (ICP-MS) to detect trace amounts of a specific element. See for example, Avella, M.; De Vlieger, J. J.; Errico, M. E.; Fischer, S.; Vacca, P.; Volpe, M. G. *Food Chem* 2005, 93, 467-474, Schmidt, B.; Petersen, J. H.; Bender Koch, C.; Plackett, D.; Johansen, N. R.; Katiyar, V.; Larsen, E. H. *Food additives & contaminants. Part A, Chemistry, analysis, control, exposure & risk assessment* 2009, 26, 1619-27, and Schmidt, B.; Katiyar, V.; Plackett, D.; Larsen, E. H.; Gerds, N.; Koch, C. B.; Petersen, J. H. *Food addit contam A* 2011, 28, 956-966. However, these methods lack the ability to track single or clustered nanoclay particles and their positions, which hampers monitoring them in time, a key aspect in modeling the transport processes.

Fluorescent labeling is a promising approach for particle tracking due to its simplicity and inherently low detection limits. See for example, Dahan, M.; Alivisatos, P.; Parak, W. J. In *Single Particle Tracking and Single Molecule Energy Transfer; Wiley-VCH Verlag GmbH & Co. KGaA*, 2009; pp. 67-96. In nanocomposites, fluorescent labels have been used to monitor nanofiller homogeneity and to characterize colloidal stability in liquids and transport. See for example, Raccurt, O.; Samuel, J.; Poncelet, O.; Szenknect, S.; Tardif, F. In *NSTI-Nanotech;* 2008; pp. 704-707. Direct incorporation of a fluorescent organic dye into layered silicates like MMT can be accomplished by ionic exchange. This approach has been used to monitor the mixing and exfoliation processes during extrusion of polymer clay nanocomposites. See for example, Maupin, P. H.; Gilman, J. W.; Harris, R. H.; Bellayer, S.; Bur, A. J.; Roth, S. C.; Murariu, M.; Morgan, A. B.; Harris, J. D. *Macromol Rapid Comm* 2004, 25, 788-792. However, the fluorescent component is not adequately coupled to the clay substrate and could easily be dislodged from the substrate during the extrusion process.

Accordingly, a new method of attaching the fluorescent component to the substrate is necessary to provide stability to the bond between the fluorescent tag and the clay.

SUMMARY OF THE INVENTION

In one aspect of the present invention, a method of detecting and tracking a stable fluorescent-labeled nanoclay, in polymer-clay nanocomposite films, and in a contact solvent after migration testing is provided. A Fluorescein-5-maleimide (fluorescein) or tetramethylrhodamine-5-maleimide (rhodamine) is covalently bonded to an organically modified montmorillonite (o-MMT). The fluorescein and rhodamine provide good thermal stability up to 220° C. and the rhodamine remained stable at 250° C. A confocal laser scanning microscopy is used to confirm the tagging and to detect the fluorescent labels in various systems.

In another aspect of the present invention, a method of monitoring a location of a nanoparticle within a nanocomposite material is provided. The method includes the steps of providing at least one nanoclay particle, attaching a fluorescent tag to the at least one nanoclay particle, and determining a fluorescence of the fluorescent-labeled nanoclay particle. The method also includes the steps of forming a nanocomposite material including the at least one fluorescent-labeled nanoclay particle, depositing the nanocomposite material in an aqueous solution, and detecting a movement of the fluorescent-labeled nanoclay particle from the nanocomposite material to the aqueous solution.

In yet another aspect of the present invention, a nanoparticle for use in a nanocomposite film is provided. The nanoparticle includes a mercaptosilane modified nanoclay platelet and a fluorescent tag attached to the mercaptosilane modified nanoclay platelet for emitting a fluorescence to determine a location of the nanoparticle.

In yet another aspect of the present invention, a nanocomposite film is provided. The nanocomposite file includes a polypropylene matrix material, a plurality of nanoclay particle coupled to the polypropylene matrix material, and a fluorescent tag attached to at least one nanoclay particle of the plurality of nanoclay. The fluorescent-tagged nanoclay particle is adapted to emit a fluorescence to facilitate determining a location of the nanoclay particle.

In one aspect of the present invention, a nanoparticle is provided. The nanoparticle includes a nanoclay particle and a fluorescent tag attached to the nanoclay particle for emitting a fluorescence to determine a location of the nanoparticle.

In another aspect of the present invention, a method of forming a nanoclay particle is provided. The method includes providing a nanoclay particle, reacting the nanoclay particle with a silane to produce a modified nanoclay particle including thiol moieties, and reacting the modified nanoclay particle with a thiol-reactive dye to form a fluorescent-labeled nanoclay particle.

BRIEF DESCRIPTION OF THE DRAWINGS

Other advantages of the present invention will be readily appreciated as the same becomes better understood by reference to the following detailed description when considered in connection with the accompanying drawings wherein:

FIG. 10a is an image of cuvettes including solvents used during a migration test, according to an embodiment of the present invention;

FIG. 10b are confocal micrograph image of residue in the cuvette shown in FIG. 10a after the migration test including fluorescent-labeled nanoclay particles, according to an embodiment of the present invention;

FIG. 13a is a confocal micrograph image of migrated residue from nanocomposite film without fluorescent-labeled nanoclay particles, according to an embodiment of the present invention;

FIG. 13b is a confocal micrograph image of migrated reside from nanocomposite film including rhodamine-labeled nanoclay particles, according to an embodiment of the present invention.

Corresponding reference characters indicate corresponding parts throughout the drawings.

DETAILED DESCRIPTION OF THE PREFERRED EMBODIMENT

With reference to the drawings and in operation, the present invention overcomes at least some of the disadvantages of known methods by providing a nanoclay particle having a fluorescent probe to facilitate monitoring a movement of the nanoclay particle with respect to a material. More specifically, the nanoclay particle may include a fluorescent tag that is covalently bonded to the nanoclay particle to provide stability to the bond between the fluorescent tag and the nanoclay particle. The fluorescent tag is adapted to emit fluorescence signals. The fluorescence signals may be detected, e.g. by using laser scanning microscopy, to facilitate determining a location of the nanoclay particle. In addition, the nanoclay particle may be adapted to be inserted into a material to facilitate monitoring a location of the nanoclay particle within the material and monitor a migration of the nanoclay particle from the material and into a surrounding environment. For example, in one embodiment, the nanoclay particle may be adapted to be coupled to a polymer-clay nanocomposite film. In another embodiment, the nanoclay particle may be formed within a biological material and/or any suitable material that enables the nanoclay particle to function as described herein. By providing a nanoclay particle that includes a fluorescent probe, the movement and position of a single and/or a cluster of nanoclay particles may be tracked to evaluate the transport of ENMs from nanocomposites and/or biological systems.

A selected embodiment of the present invention will now be explained with reference to the drawings. It will be apparent to those skilled in the art from this disclosure that the following description of the embodiment of the present invention is provided for illustration only and not for the purpose of limiting the invention as defined by the appended claims and their equivalents.

Figure 1:
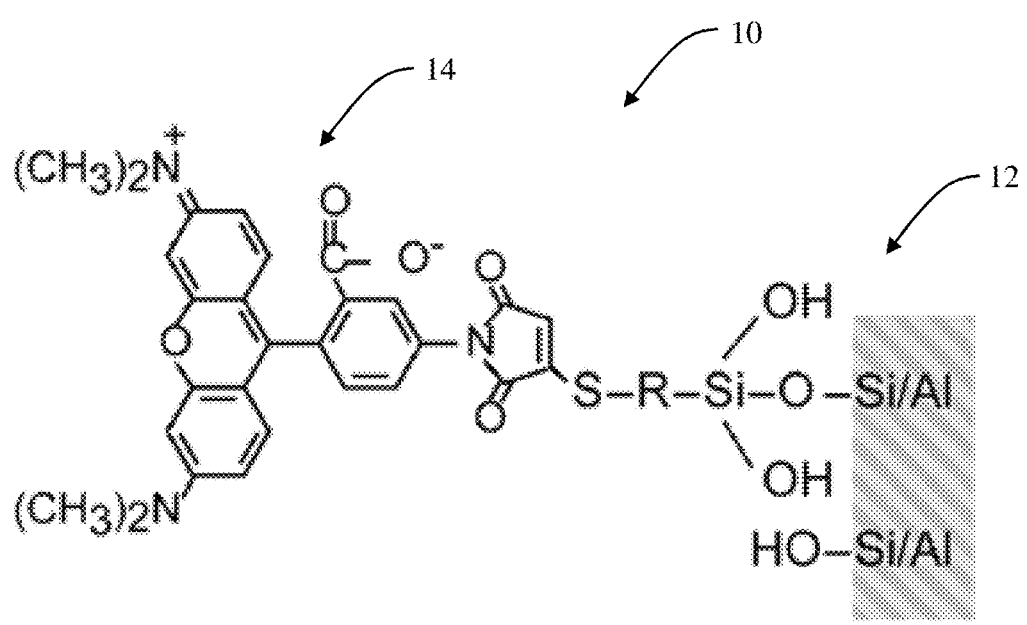
FIG. 1 a schematic diagram of a nanoparticle, according to an embodiment of the present invention.

FIG. 1 a schematic diagram of an engineered nanomaterial 10 including a fluorescent-labeled nanoparticle, according to an embodiment of the present invention. In the illustrated embodiment, the fluorescent-labeled nanoparticle 10 includes a nanoclay particle 12 and a fluorescent tag 14 that is covalently bonded to the nanoclay particle 12. In one embodiment, the nanoclay particle 12 includes an organically modified montmorillonite. The nanoclay particle 12 may also include a silane-treated nanoclay such as, for example, a mercaptosilane modified nanoclay platelet. In the illustrated embodiment, the fluorescent tag 14 is selected from a group of fluorescence including fluorescein and/or rhodamine. For example, in one embodiment, the fluorescein may include fluorescein-5-maleimide. In another embodiment, the rhodamine may include tetramethylrhodamine-5-maleimide. In addition, fluorescent tag 14 may also include any other equivalent fluorescence probe and/or any suitable material and/or compound that facilitates determining a location and/or a movement of the engineered nanomaterial 10. In the illustrated embodiment, the fluorescent tag 14 is attached to the nanoclay particle 12 with a covalent bond to resist detachment of the fluorescent tag 14 during additional processing. For example, in one embodiment, the fluorescent-labeled nanoparticle 10 may be used to form a nanocomposite film. The covalent bond enables the fluorescent tag 14 to remain attached to the nanoclay particle 12 during the formation of the nanocomposite film.

In the illustrated embodiment, the fluorescent tag 14 is adapted to emit fluorescence signals that may be detected using confocal laser scanning microscopy (CLSM) to facilitate determining a location of the fluorescent-labeled nanoparticle 10 within the matrix material and/or a migration of the fluorescent-labeled nanoparticle 10 from the matrix material to a surrounding environment. In one embodiment, the fluorescent-labeled nanoparticle 10 may be adapted to be coupled to a polymer-clay nanocomposite film. In another embodiment, the fluorescent-labeled nanoparticle 10 may be formed within a biological material and/or any suitable material that enables the fluorescent-labeled nanoparticle 10 to function as described herein.

In one embodiment, the nanocomposite film may include a polypropylene matrix material and one or more fluorescent-labeled nanoparticles 10 that are coupled to the matrix material. In another embodiment, the nanocomposite film may include a plurality of nanoclay particles that are coupled to the polypropylene matrix, and a fluorescent tag 14 that is attached to at least one of the nanoclay particles to emit a fluorescence to facilitate determining a location of the fluorescent tagged nanoclay particle.

Figure 2:
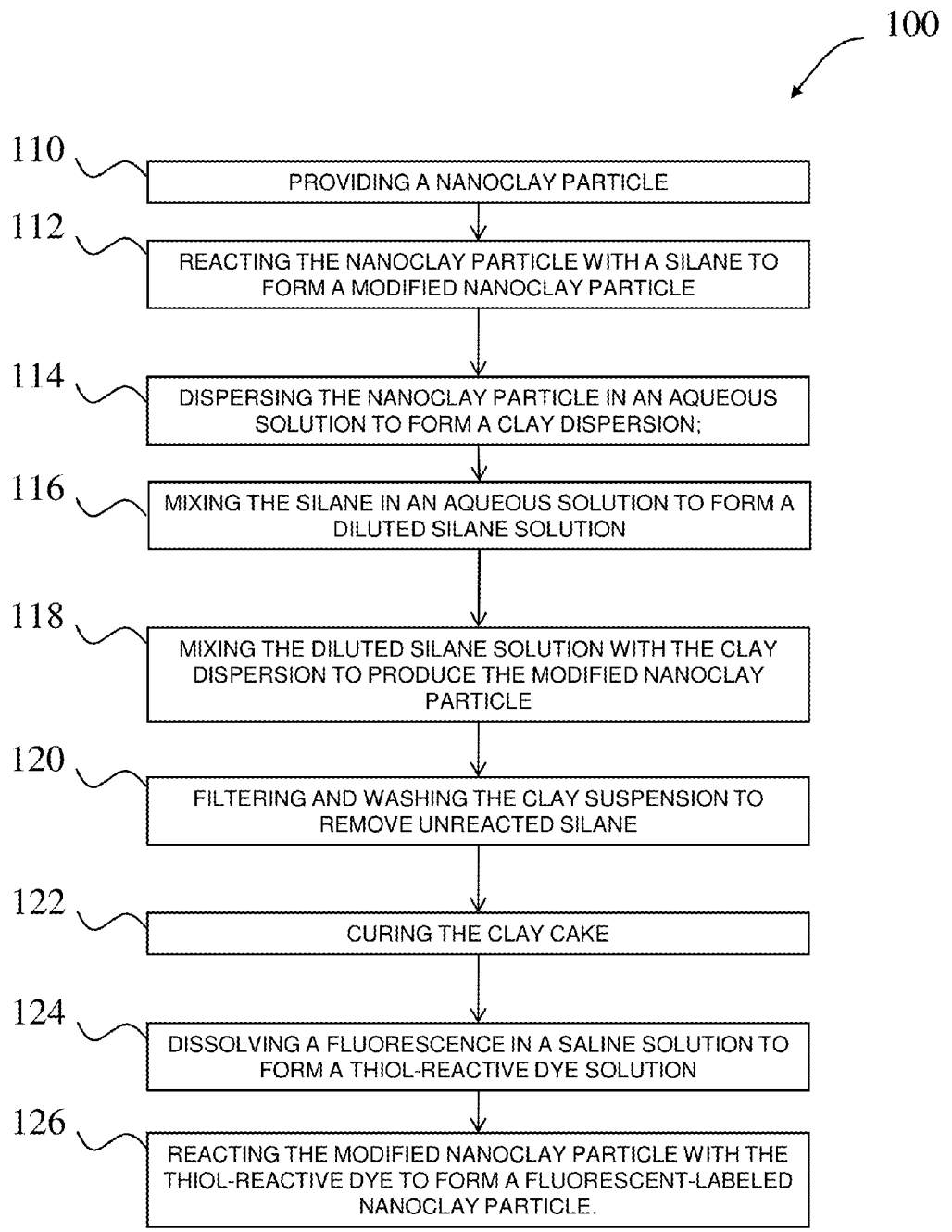
FIG. 2 is a flowchart of an exemplary method of forming the nanoparticle shown in FIG. 1 including attaching a fluorescent label to a nanoclay, according to an embodiment of the present invention.
Figure 3:
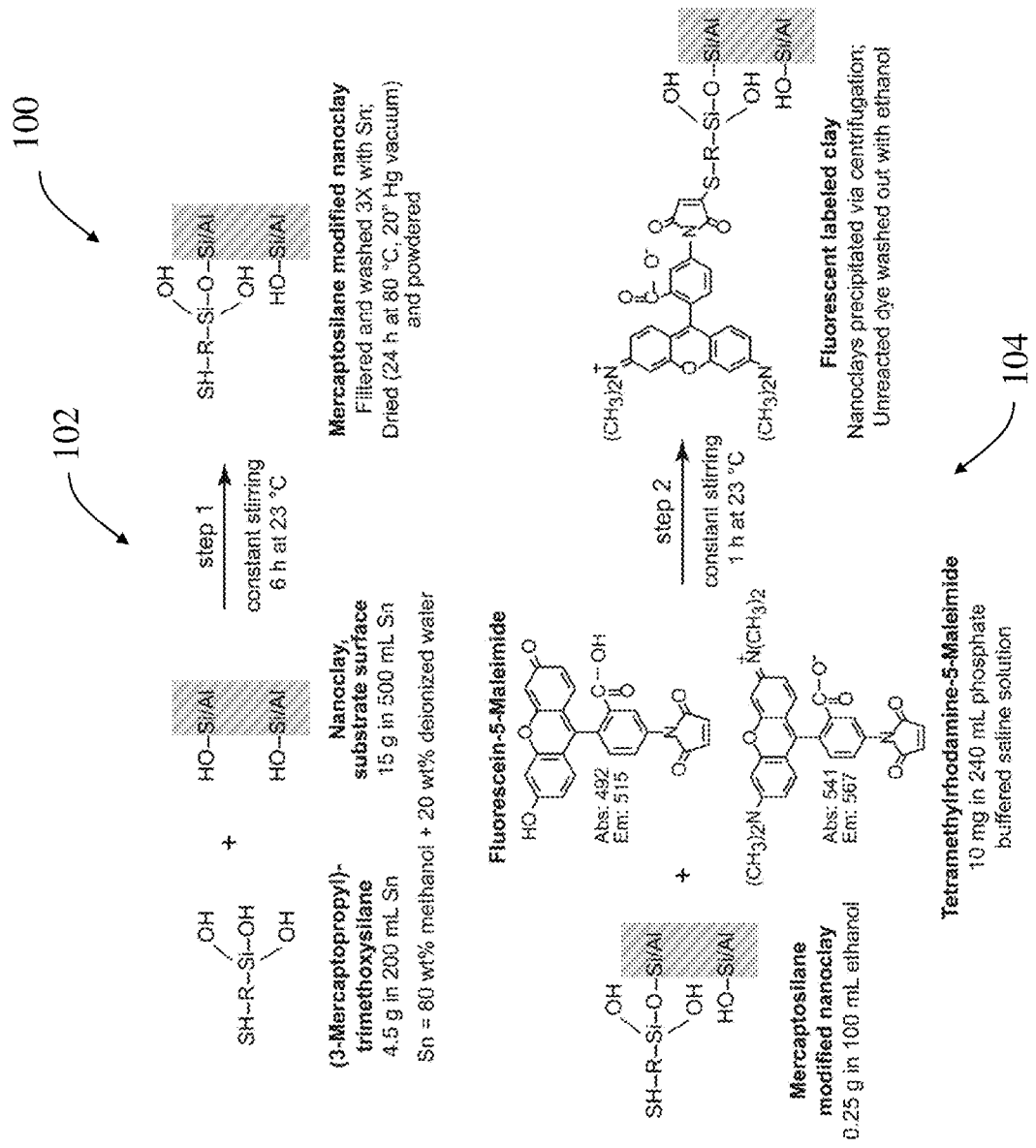
FIG. 3 is a schematic representation of a method of attaching a fluorescent label to a nanoclay, according to an embodiment of the present invention.

FIG. 2 is a flowchart of an exemplary method 100 that may be used to form the engineered nanoparticle 10 shown in FIG. 1. FIG. 3 is a schematic representation of the method 100. Each method step may be performed independently of, or in combination with, other method steps. In general, the method 100 includes a silylation step 102 and a conjugation step 104. The silylation step 102 includes a silane treatment of nanoclay to convert hydroxyl groups into thiol moieties to form a silane-modified nanoclay. The conjugation step 104 includes fluorescent dye conjugation with the silane-modified nanoclay to form a fluorescent labeled clay.

In the illustrated embodiment, during the silylation step 102, a nanoclay platelet is reacted with a silane to form a silane treated nanoclay platelet. In one embodiment, the nanoclay platelet is reacted with a mercaptosilane. The hydroxyls on the edges of the nanoclay platelets are converted into thiol moieties in the presence of a mercaptosilane to form a mercaptosilane modified nanoclay particle. The silylation reaction is carried out in an aqueous methanol solution. Additional details of a silylation procedure, which may be used in the present invention, are described in U.S. patent application Ser. No. 12/780,461 to Jayaraman et al., U.S. Patent Publication No. 2010/0310802, filed May 14, 2010, titled "Novel Nanocomposites and Nanocomposite Foams and Methods and Products Related to Same", which is incorporated herein by reference in its entirety.

During the conjugation step 104, a thiol-reactive dye such as, for example, a fluorescein-5-maleimide (fluorescein) and/or a tetramethylrhodamine-5-maleimide (rhodamine), is reacted with the silane-treated nanoclay. The selection of the fluorescent tag is based on label photostability, high extinction coefficients and high fluorescence quantum yield. The thiol-reactive group (i.e., maleimide) allows the reaction to be carried out at neutral pH with high selectivity and promoted the development of a covalent bond.

In the illustrated embodiment, the method 100 includes providing 110 a nanoclay particle 12 such as, for example, an organically modified montmorillonite (o-MMT), and reacting 112 the nanoclay particle 12 with a silane to form a modified nanoclay particle including thiol moieties. The o-MMT nanoclay particle is dispersed 114 in an aqueous solution to form a clay dispersion. In one embodiment, the aqueous solution may include a solvent including methanol and deionized water. The silane is mixed 116 in an aqueous solution to form a diluted silane solution. Moreover, the silane is diluted using a similar solvent including methanol and deionized water. In one embodiment, the silane includes mercaptosilane.

In the illustrated embodiment, the diluted silane solution is mixed 118 with the clay dispersion to facilitate reacting the nanoclay particle with a silane to produce the modified nanoclay particle. Moreover, the diluted silane solution is slowly added to the clay dispersion and stirred for predefined period of time at a predefined temperature to facilitate reacting the nanoclay particle with a silane. The clay suspension is then filtered 120 and washed using the solvent to remove unreacted silane to form a clay cake. The clay cake is then cured 122 to form a clay cake including the modified nanoclay particle. In one embodiment, the clay suspension is filtered and washed using the solvent including methanol and deionized water, and the resulting clay cake is dried for a predefined period of time under a vacuum. The cured clay cake is then powdered and shaken through a sieve. In one embodiment, the cured clay cake is powdered using a mortal and pestle and shaken though a No. 200 sieve (75 µm).

In the illustrated embodiment, the method 100 may also include dissolving 124 a fluorescence in a saline solution to form a thiol-reactive dye solution, and reacting 126 the modified nanoclay particle with the thiol-reactive dye to form a fluorescent-labeled nanoclay particle.

Moreover, the method 100 may include dissolving the cured clay cake including the modified nanoclay particle in an alcohol solution and mixing the saline solution including the fluorescence dye with the alcohol solution to facilitate reacting the fluorescence probe with the modified nanoclay particle to form the fluorescent-labeled nanoclay particle. The fluorescent-labeled nanoclay particle is then separated from the mixed solution with centrifuging.

In one embodiment, the saline solution may include a phosphate buffered saline (PBS) solution. Moreover, the alcohol solution may include ethanol. In addition, in one embodiment, the fluorescent dye may include a fluorescein-based dye that is dissolved directly in PBS. In another embodiment, the fluorescent dye may include a rhodamine-based dye that is first dissolved in methanol to form a stock solution, and then the stock solution is dissolved in PBS. In the illustrated embodiment, the modified nanoclay (treated with mercaptosilane) is dissolved in ethanol and carefully added to the PBS solution containing the fluorescent dye. The resultant solution is shaken and stirred with a magnetic stirrer for about 1 hour (incubation time). The clay is then separated from the solution by centrifuging to form clay pellets. The clay pellets including the fluorescent-labeled nanoclay particles are then washed in ethanol and centrifuged. The washing cycle is repeated until a clear solution is obtained.

Figure 4:
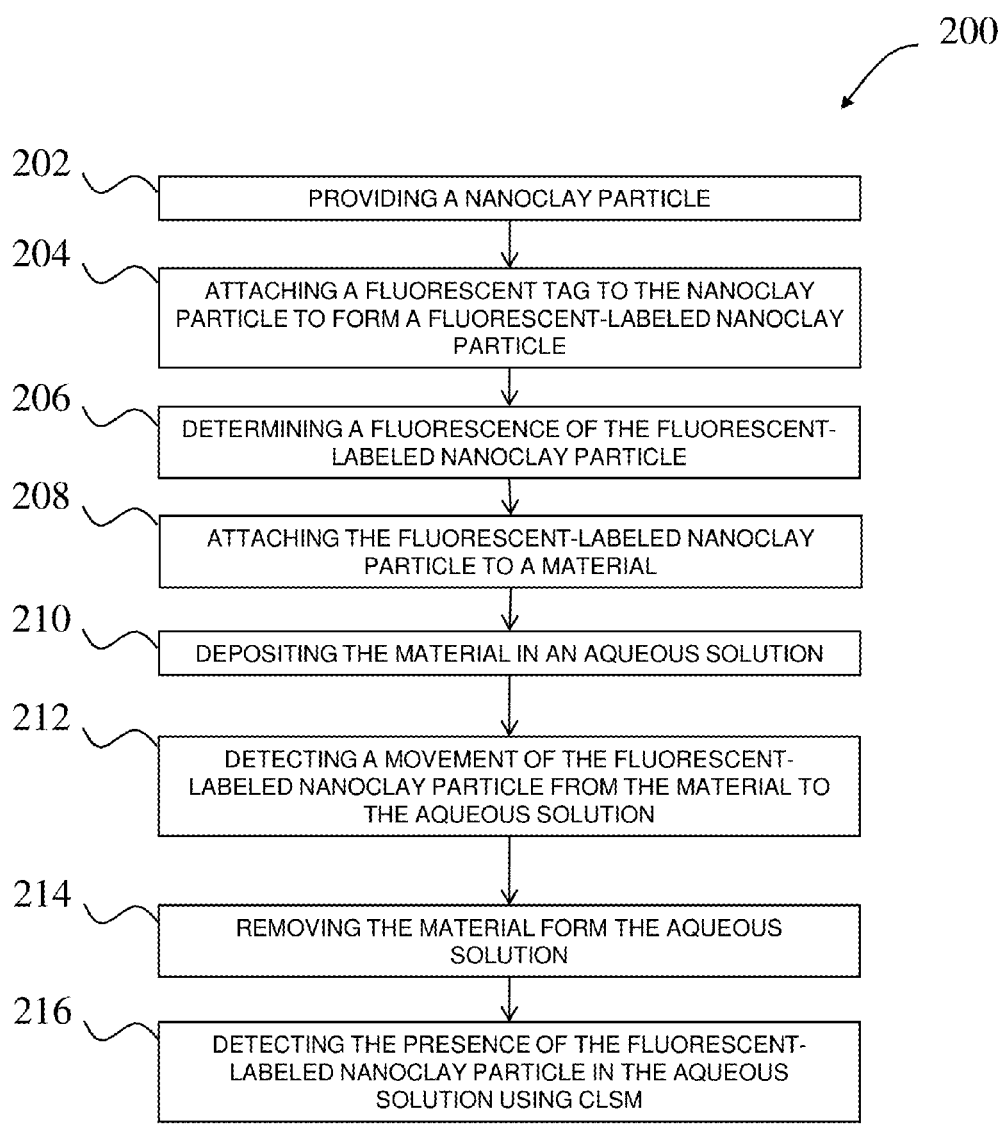
FIG. 4 is a flow chart of an exemplary method of monitoring a location of a nanoparticle within a material, according to an embodiment of the present invention.
Figure 5:
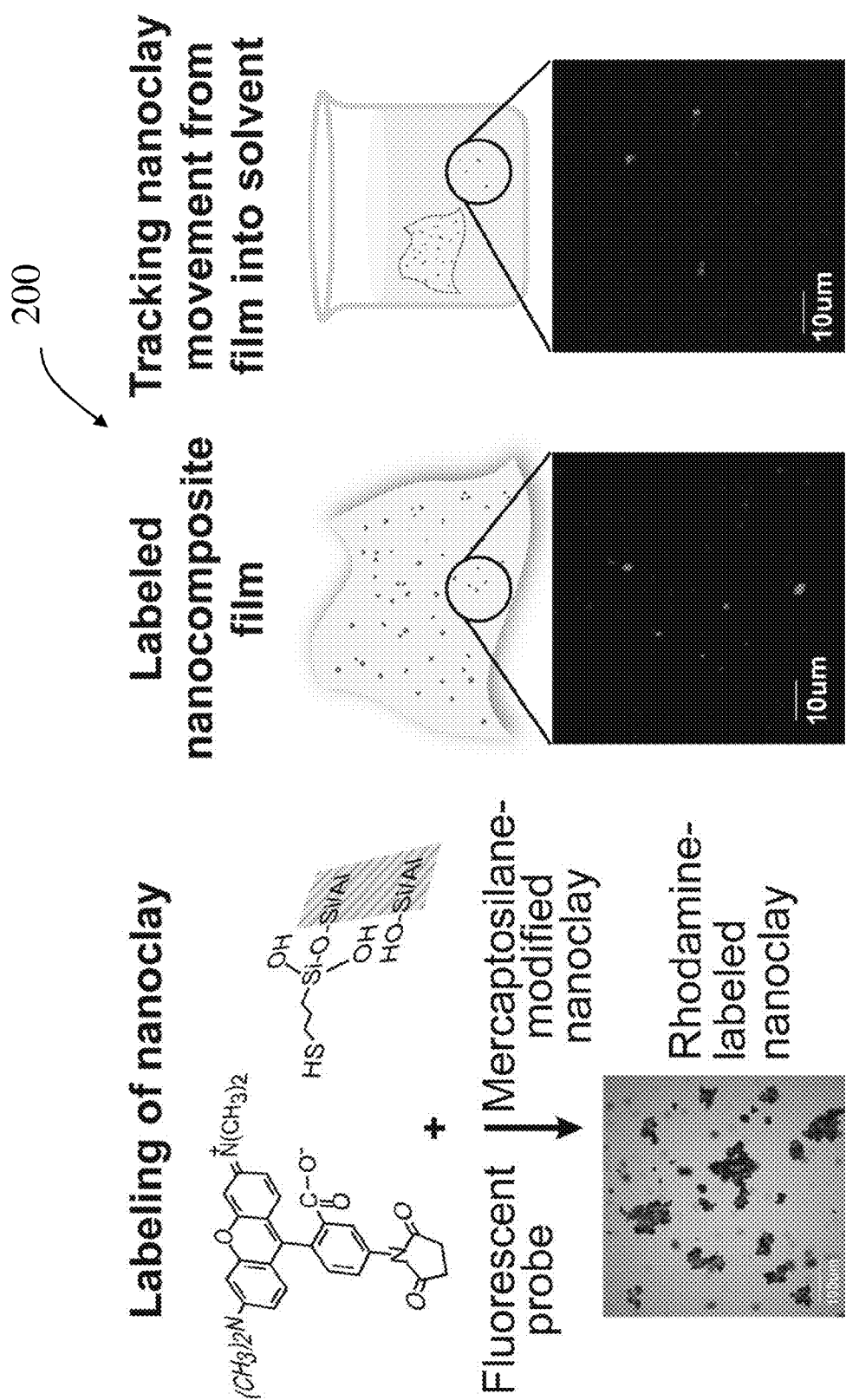
FIG. 5 is a schematic representation of a method of detecting a migration of nanoclay particles from a nanocomposite film to a solvent, according to an embodiment of the present invention.

FIG. 4 is a flow chart of an exemplary method 200 of monitoring a location of a nanoparticle within a material, according to an embodiment of the present invention. FIG. 5 is a schematic representation of the method 200. Each method step may be performed independently of, or in combination with, other method steps. In the illustrated embodiment, the method 200 includes providing 202 at least one nanoclay particle 12 and attaching 204 a fluorescent tag to the at least one nanoclay particle to form a fluorescent-labeled nanoclay particle. In one embodiment, the method 200 may include providing a nanoclay platelet, reacting the nanoclay platelet with a mercaptosilane to produce a mercaptosilane modified nanoclay particle including thiol moieties, and reacting the mercaptosilane modified nanoclay particle with a thiol-reactive dye to form the fluorescent-labeled nanoclay particle.

The method 200 also includes determining 206 a fluorescence of the fluorescent-labeled nanoclay particle. Moreover, the fluorescent-labeled nanoclay particle is adapted to emit fluorescence signals. In one embodiment, confocal laser scanning microscopy may be used to detect the presence of fluorescent-labeled nanoclay particle and determine the fluorescence of the fluorescent-labeled nanoclay particle. For example, in one embodiment, the fluorescent-labeled nanoclay particle may include fluorescein. In another embodiment, the fluorescent-labeled nanoclay particle may include rhodamine and/or and any other equivalent fluorescence probe.

In the illustrated embodiment, the method 200 includes attaching 208 the fluorescent-labeled nanoclay particle to the material, depositing 210 the material in an aqueous solution, and detecting 212 a movement of the fluorescent-labeled nanoclay particle from the material to the aqueous solution. The material may include a polymeric material, a biological material, and/or any suitable material that may be formed with the fluorescent-labeled nanoclay particle. In one embodiment, the method 200 may also include providing a polypropylene matrix material, mixing the fluorescent-labeled nanoclay particle with the polypropylene matrix material, and extruding the mixture to form a nanocomposite material.

In the illustrated embodiment, the method 200 includes removing 214 the material form the aqueous solution; and detecting 216 the presence of the at least one fluorescent-labeled nanoclay particle in the aqueous solution using CLSM.

EXAMPLE 1

In the illustrated embodiment, the present invention describes a new methodology to detect and track stable fluorescent-labeled o-MMT in a polymer-clay nanocomposite after film manufacture and preliminary mass transport-migration testing. First, two fluorescent tags were selected that could form covalent bonds with o-MMT upon the functionalization of the nanoclay substrate. Second, the thermal stability of the fluorescent-labeled o-MMT was studied at high temperatures to simulate melt-processing conditions used in polymer film manufacture. Third, the fluorescent-labeled o-MMT was incorporated into a model polymer (polypropylene) matrix. The nanocomposite films were manufactured and the fluorescence of the films was detected. Finally, a preliminary mass transport-migration test was carried out by exposing the nanocomposite films to ethanol at 80° C. and evaluating the solvent for trace amounts of labeled o-MMT.

In the illustrated embodiment, the nanoclay is labeled with either fluorescein-5-maleimide (fluorescein) or tetramethylrhodamine-5-maleimide (rhodamine) following the same procedure.

In the silylation step, the hydroxyls on the edges of the nanoclay platelets are converted into thiol moieties in the presence of a mercaptosilane. The reaction is carried out in an aqueous methanol solution.

In the conjugation step, a thiol-reactive dye, either fluorescein-5-maleimide (fluorescein) or tetramethylrhodamine-5-maleimide (rhodamine), is reacted with the silane-treated nanoclay. The selection of the fluorescent tag is based on label photostability, high extinction coefficients and high fluorescence quantum yield. The thiol-reactive group (i.e., maleimide) allows the reaction to be carried out at neutral pH with high selectivity and promoted the development of a covalent bond.

Confocal laser scanning microscopy (CLSM) is used for the detection of fluorescent-labeled nanoclays because this technique has the ability to detect spatially resolved emission intensities and the capability to analyze emission intensity as a function of the z-position. (See for example, Hoffmann, K.; Mix, R.; Friedrich, J. F.; Resch-Genger, U. In *Reviews in Fluorescence* 2008; Geddes, C. D., Ed.; Springer New York: New York, N.Y., 2010; pp. 139-160). Confocal images can yield quantitative information with an optical resolution approaching 200 nm, and are well suited for detection of fluorescent particles and also to track movement in different medium. (See for example, Nashat, A. H.; Moronne, M.; Ferrari, M. *Biotechnol Bioeng* 1998, 60, 137-146). New single-particle tracking (SPT) techniques have been developed in the last decade, which may help in the future detect nanoparticles that have smaller aspect ratio than o-MMT. In addition, confocal microscopy-aided spectrophotometric analysis is used to characterize the emission spectra of the labeled samples.

Figure 6A:
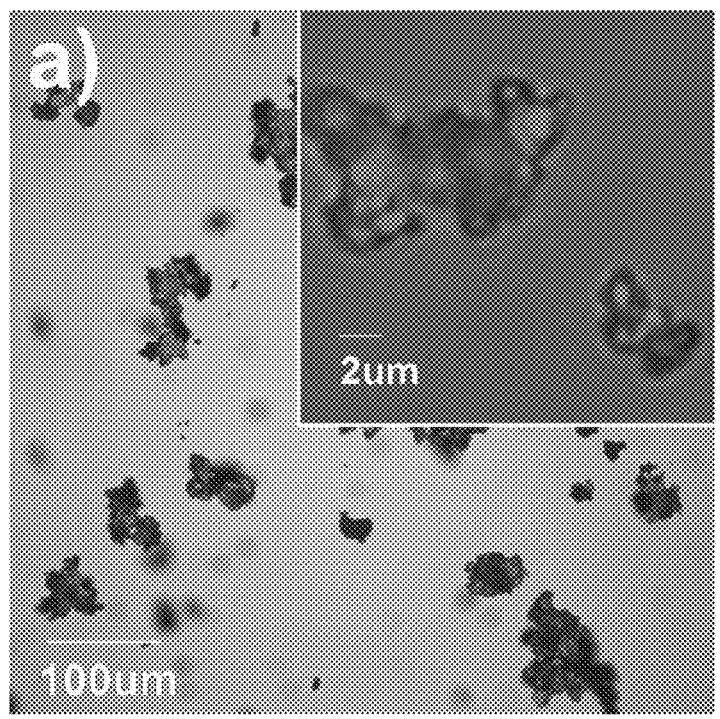
FIG. 6a is a confocal micrograph image of nanoclay particles with fluorescent tags including rhodamine, according to an embodiment of the present invention.
Figure 6B:
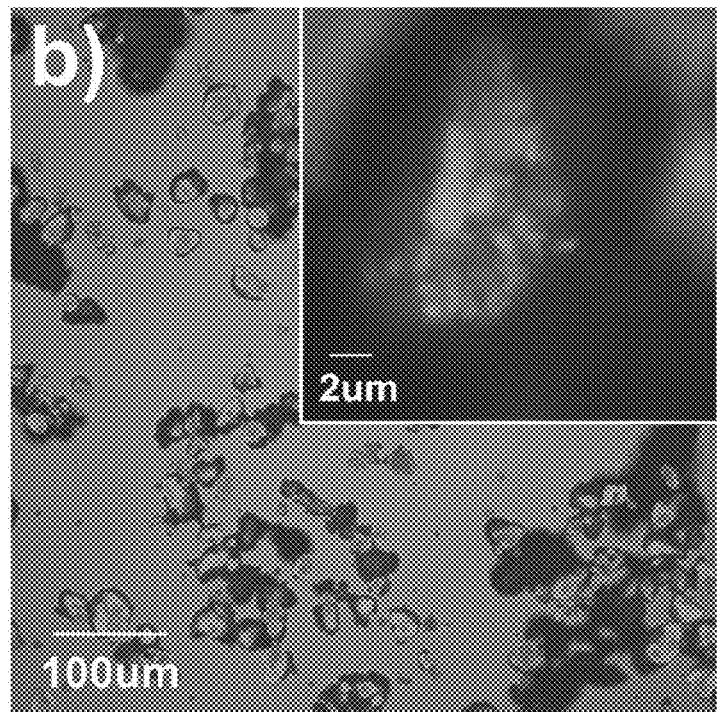
FIG. 6b is a confocal micrograph image of nanoclay particles with fluorescent tags including fluorescein, according to an embodiment of the present invention.
Figure 6C:
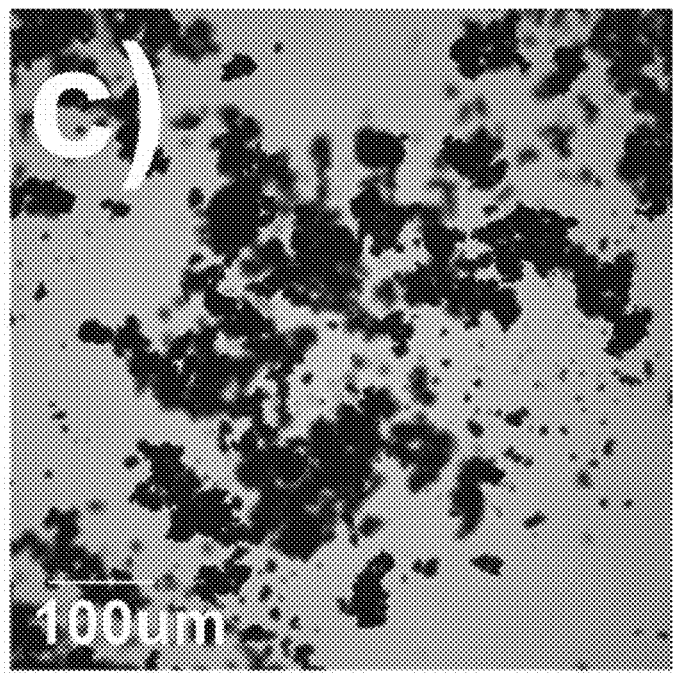
FIGS. 6c and 6d are confocal micrograph images of nanoclay particles without fluorescent tags.
Figure 6D:
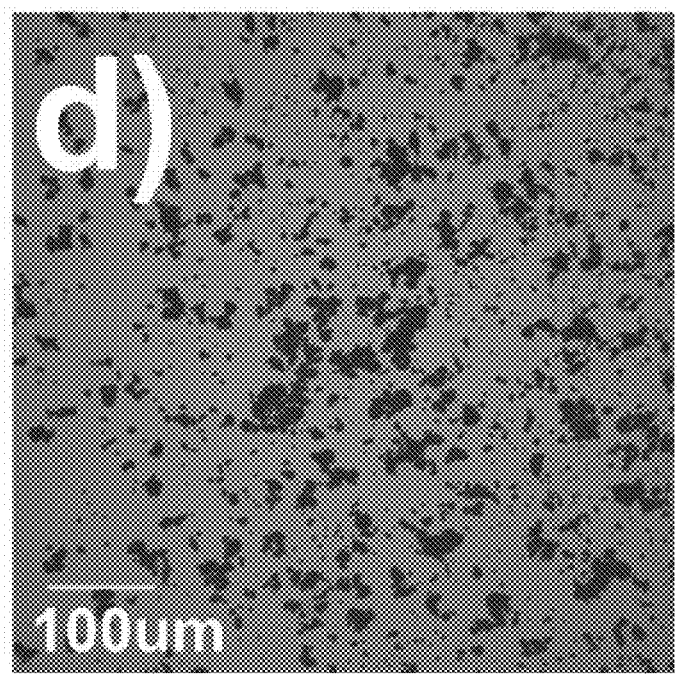

FIG. 6a is a confocal micrograph image of nanoclay particles with fluorescent tags including rhodamine. FIG. 6b is a confocal micrograph image of nanoclay particles with fluorescent tags including fluorescein. FIGS. 6c and 6d are confocal micrograph images of nanoclay particles without fluorescent tags. In the illustrated embodiment, FIGS. 6a-6d are confocal micrographs showing nanoclay and clustered nanoclays with fluorescent tags, (a) rhodamine (shown in FIG. 6a) and (b) fluorescein (shown in FIG. 6b), and without fluorescent tags, (c) and (d), respectively (shown in FIGS. 6c and 6d). Micrographs (a, c) and (b, d) were taken using the same parameters. The images are acquired using an Olympus FluoView FV1000 confocal laser scanning microscope configured on a fully automated inverted IX81 microscope. The fluorescence is excited using 543 nm (a, c) (shown in FIGS. 6a and 6c) and 488 nm (b, d) lasers (shown in FIGS. 6b and 6d). A red fluorescence signal from the rhodamine is captured using a 560 long pass emission filter and a green fluorescence signal from the fluorescein is captured using a 505-525 nm band pass emission filter. The transmitted light image was generated in a brightfield mode.

In FIGS. 6a through 6d, CLSM images of the rhodamine- and fluorescein-labeled nanoclays and unlabeled counterparts show a clear distinction between the labeled and unlabeled nanoclays. In the illustrated embodiment, the fluorescence signals in red (FIG. 6a) and green (FIG. 6b) confirm the presence of rhodamine and fluorescein, respectively, attached to the nanoclay.

Before attempting to track the fluorescent-labeled nanoclays in polymer nanocomposites, it is important to understand the effect of polymer processing temperatures on the fluorescence intensity and stability. Processing of polymer systems involves melt mixing and forming at melting temperatures of 150-250° C. High temperatures may prompt clay-dye and dye-dye interactions as well as changes in the microenvironment, which can result in modulations of the absorption and emission properties as well as fluorescence quenching. (See for example, Hoffmann, K.; Mix, R.; Friedrich, J. F.; Resch-Genger, U. In *Reviews in Fluorescence* 2008; Geddes, C. D., Ed.; Springer New York: New York, N.Y., 2010; pp. 139-160). The labeled nanoclay powder is exposed to 220 and 250° C. for 15 minutes under a continuous purge of nitrogen (60 mL/min). After heating, the samples are mounted on a glass microscope slide for confocal analysis to determine the stability of the fluorescent labels as a function of temperature.

Figure 7A:
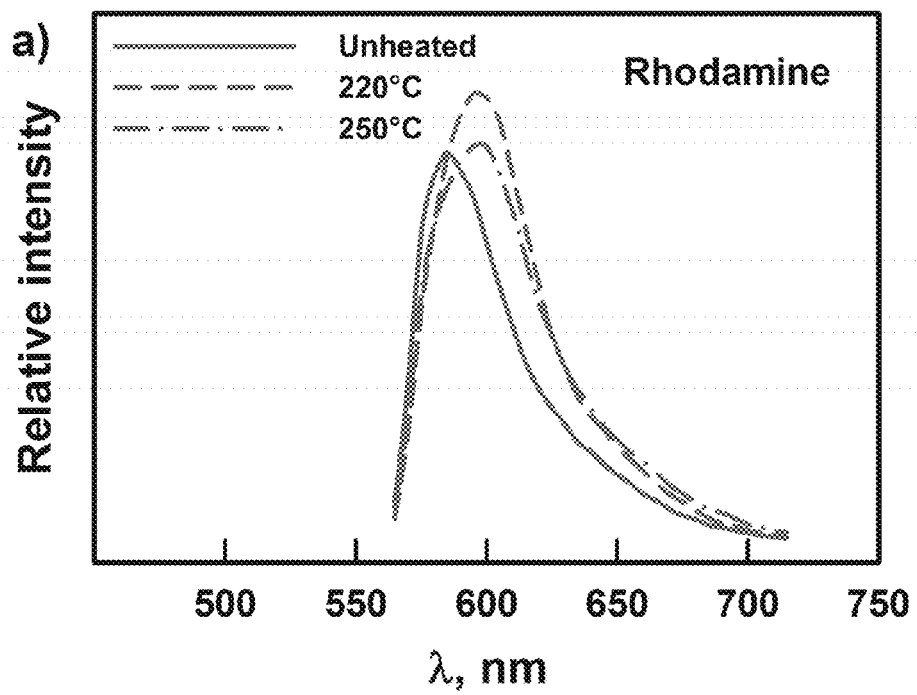
FIG. 7a is a graph illustrating fluorescence emission spectra including excitation wavelengths of rhodamine-labeled nanoclay shown in FIG. 6a before and after exposure to 220° C. and 250° C., according to an embodiment of the present invention.
Figure 7B:
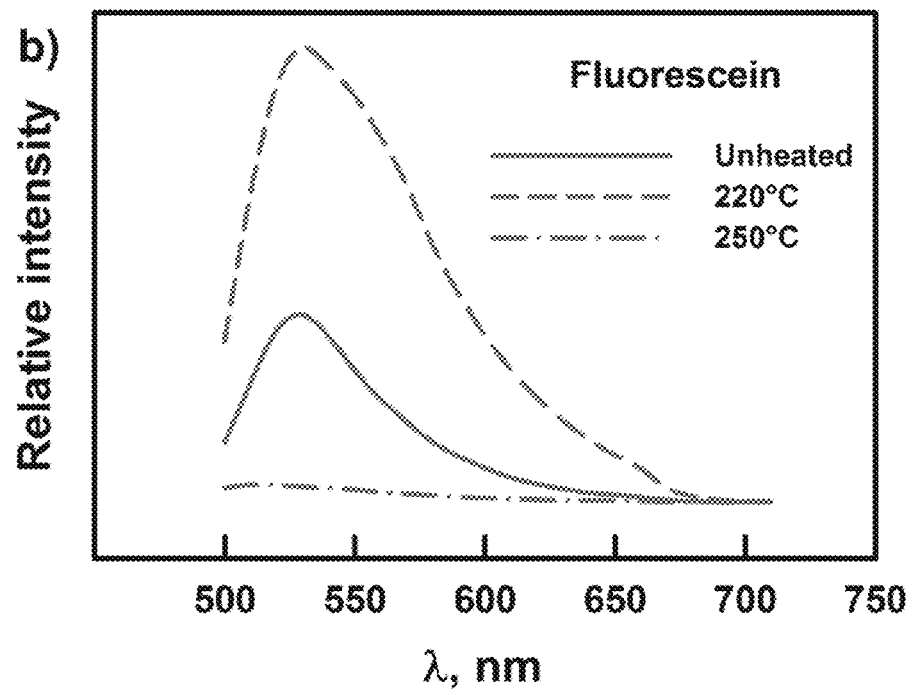
FIG. 7b is a graph illustrating fluorescence emission spectra including excitation wavelengths of fluorescein-labeled nanoclay shown in FIG. 6b before and after exposure to 220° C. and 250° C., according to an embodiment of the present invention.

FIG. 7a is a graph illustrating fluorescence emission spectra including excitation wavelengths of rhodamine-labeled nanoclay shown in FIG. 6a before and after exposure to 220° C. and 250° C. FIG. 7b is a graph illustrating fluorescence emission spectra including excitation wavelengths of fluorescein-labeled nanoclay shown in FIG. 6b before and after exposure to 220° C. and 250° C. FIGS. 7a and 7b show fluorescence emission spectra of (a) rhodamine-labeled and (b) fluorescein-labeled nanoclay before and after exposure to 220° C. and 250° C. for 15 minutes. The excitation wavelengths are 543 nm (a) and 488 nm (b). Nanoclay samples are heated in a TGA furnace from room temperature and isothermally maintained at the set temperature for 15 minutes. Changes in emission spectra are quantified using the relative integral fluorescence emission (RIFE) parameter. For rhodamine: RIFE no heat=1.00±0.14A, RIFE 220° C.=1.31±0.35A, RIFE 250° C.=1.35±0.17A. For fluorescein: RIFE no heat=1.00±0.08A, RIFE 220° C.=3.60±0.58B, RIFE 250° C.=0.34±0.10C. The mean values with different uppercase superscripts are significantly different (p<0.05) according to Tukey's HSD test.

In the illustrated embodiment, FIGS. 7a and 7b show the emission spectra of the two labeled nanoclays before and after the exposure to 220° C. and 250° C. The heated and unheated rhodamine-labeled nanoclay had similar emission patterns. For the rhodamine-labeled samples, exposure to 220° C. and 250° C. resulted in only a slight shift of the emission peaks towards a higher wavelength, with minimum changes in fluorescence intensity. The relative integral fluorescence emission (RIFE) was not significantly different at either exposure temperature. On the other hand, the emission patterns of the fluorescein-labeled nanoclay showed a significant increase in fluorescence intensity for those samples exposed to 220° C. and a complete drop at 250° C. Raising the temperature likely affected the chemical structure of the fluorophore, causing fluorescence enhancement at 220° C. and quenching at 250° C. This effect was quantified by the RIFE parameter, which increased from about 1 to about 3.6 at 220° C. and decreased to about 0.34 at 250° C. The results indicated that the fluorescein tag is more heat sensitive than the rhodamine tag. Both labels showed good thermal stability at 220° C., but only the rhodamine label remained stable at 250° C.

To prepare the polymer-clay nanocomposite, the fluorescent-labeled o-MMT is introduced in a polypropylene (PP) matrix through melt blending in an internal mixer. Films are made via compression molding from preblended nanocomposite granulates. PP and nanoclay are a good nanocomposite model system because both components are extensively used in consumer and non-consumer goods and packaging applications. This technique can be expanded to other common polymers such as nylon, poly(ethylene-terephthalate), and poly(lactic acid). The PP is blended with about 3 wt % nanoclay and about 12 wt % compatibilizer (maleic anhydride modified polypropylene) to enhance dispersion of the nanoclay.

Figure 8A:
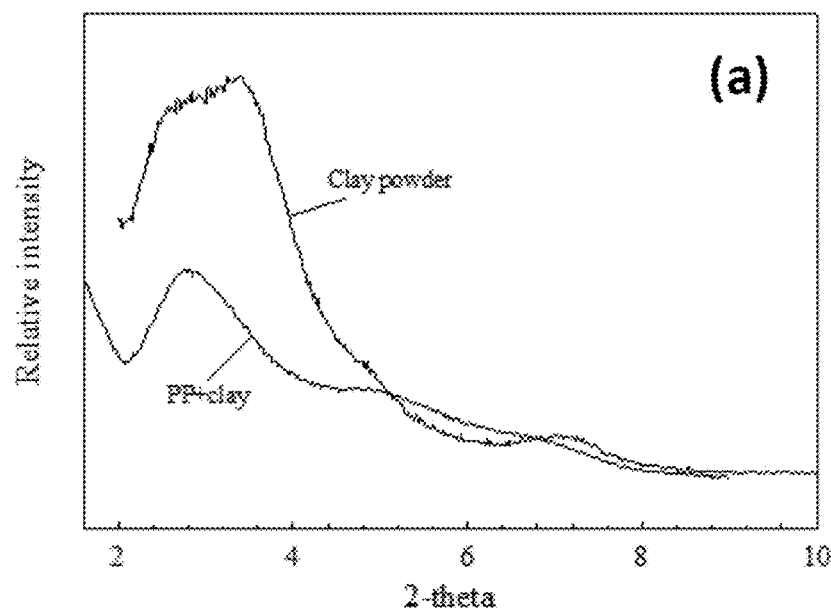
FIG. 8a is a graph illustrating XRD patterns for a nanoclay and a nanocomposite, respectively.
Figure 8B:
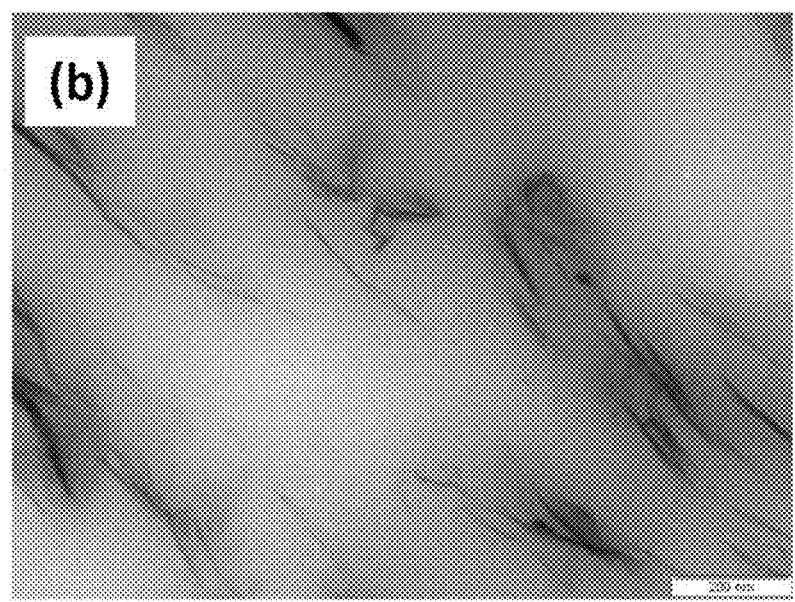
FIG. 8b is a TEM micrograph image of a nanocomposite showing intercalated and exfoliated structures.

FIG. 8a is a graph illustrating XRD patterns for a nanoclay and a nanocomposite, respectively. FIG. 8b is a TEM micrograph image of a nanocomposite showing intercalated and exfoliated structures. In the illustrated embodiment, FIGS. 8a and 8b show PP-clay nanocomposite characterization. FIG. 8a illustrates (a) XRD patterns for nanoclay and nanocomposite. FIG. 8b illustrates (b) TEM micrograph of nanocomposite showing intercalated and exfoliated structures. FIGS. 8a and 8b show the morphology of the nanocomposite as observed by X-ray diffraction (XRD) and transmission electron microscopy (TEM). Labeled and unlabeled nanocomposite films are prepared: the labeled nanocomposite films includes about 15 wt % of either fluorescein- or rhodamine-labeled o-MMT based on the total amount of clay (3 wt %).

Figure 9A:
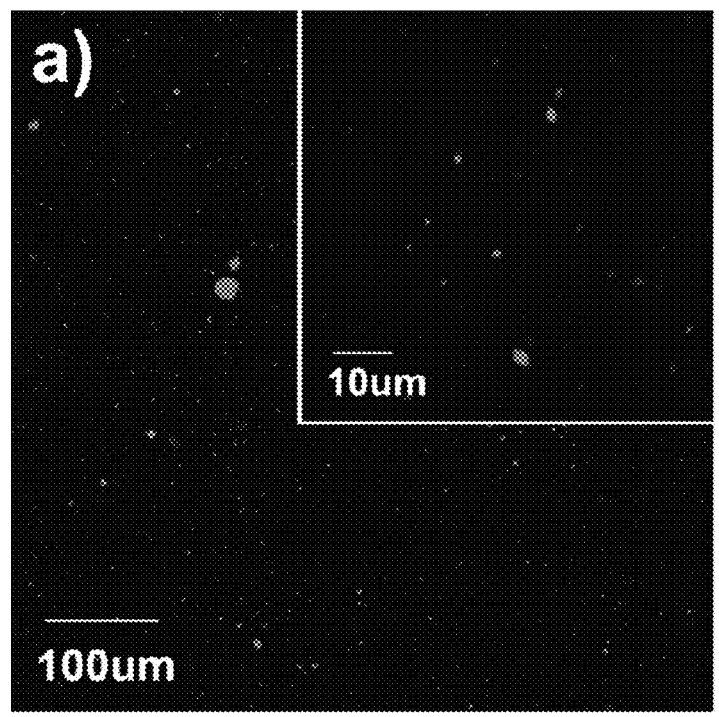
FIG. 9a are confocal micrograph images of a rhodamine-labeled nanocomposite film, according to an embodiment of the present invention.
Figure 9B:
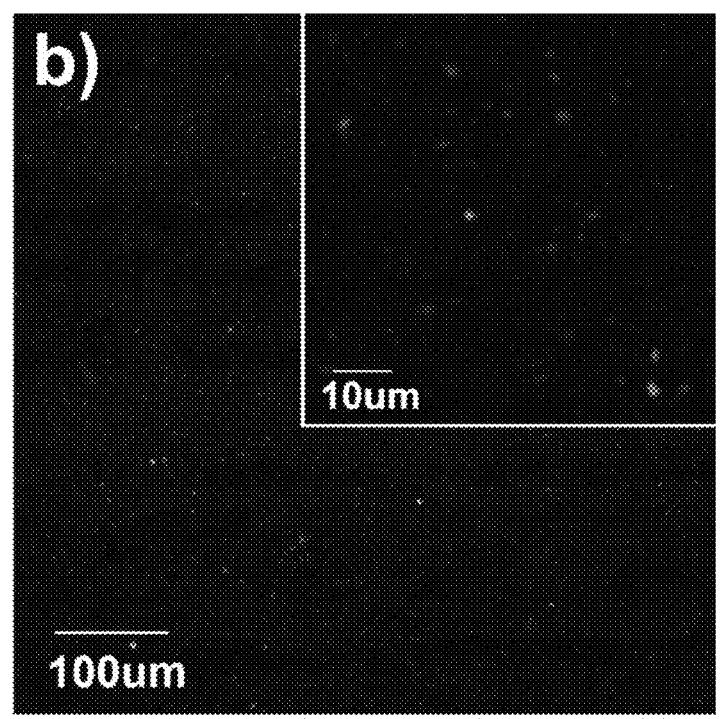
FIG. 9b are confocal micrograph images of a fluorescein-labeled nanocomposite film, according to an embodiment of the present invention.
Figure 9C:
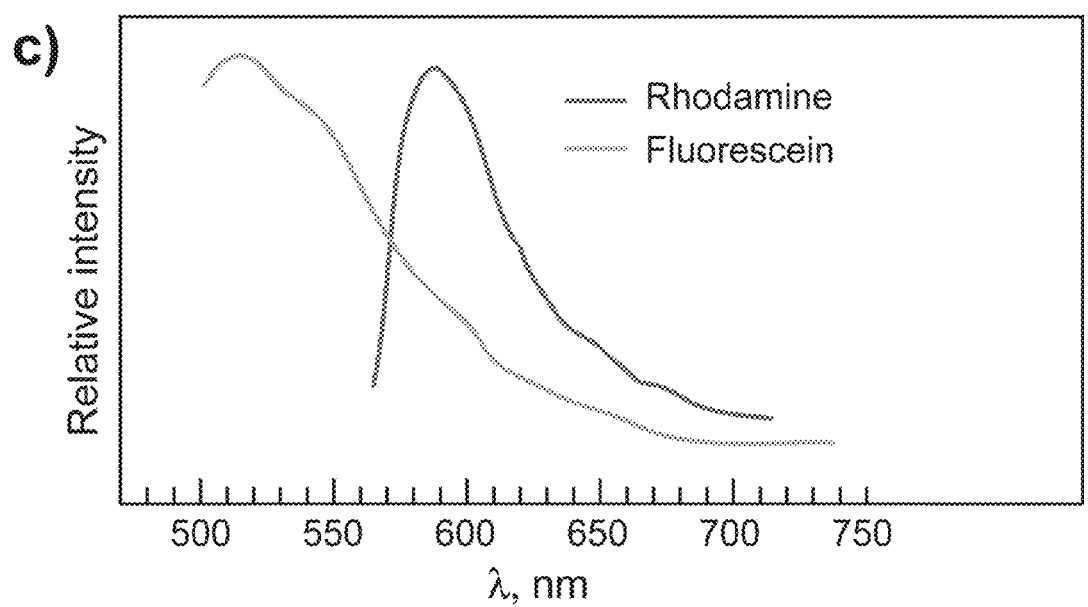
FIG. 9c is a graph illustrating fluorescence emission spectra including excitation wavelengths of the rhodamine-labeled nanocomposite film shown in FIG. 9a and the fluorescein-labeled nanocomposite film shown in FIG. 9b, according to an embodiment of the present invention.

Confocal micrographs showing evidence of both fluorescent tags in the labeled nanoclays in the nanocomposite films are provided in FIGS. 9a through 9c. FIG. 9a are confocal micrograph images of a rhodamine-labeled nanocomposite film. FIG. 9b are confocal micrograph images of a fluorescein-labeled nanocomposite film. FIG. 9c is a graph illustrating fluorescence emission spectra including excitation wavelengths of the rhodamine-labeled nanocomposite film shown in FIG. 9a and the fluorescein-labeled nanocomposite film shown in FIG. 9b. In the illustrated embodiment, FIGS. 9a and 9b illustrate confocal micrographs of (a) rhodamine-labeled and (b) fluorescein-labeled nanocomposite films (85 wt % PP, 3 wt % nanoclay, 12 wt % MAPP). Films of ~100 μm thickness are prepared from melt-mixed pellets via compression molding (175° C., 10 tons) using a Teflon mold. The mixing is performed on an internal mixer heated at 180° C. for 6 minutes at 80 rpm under nitrogen atmosphere. FIG. 9c illustrates (c) emission spectra of the bright particles in (a) and (b). The emission intensity depends on the concentration of fluorophores, thus the bright particles indicated a cluster of fluorescent dye molecules attached to the nanoclay. If the dye molecules were to disassociate from the nanoclay, the dye would be more diluted and thus the emission intensity would be dimmer. The detection limit depends on the specific fluorophore (i.e., extinction coefficient and quantum yield) and the parameters in the confocal apparatus. A typical limit of detection of fluorescence in solution is in the order of about 10-12 mol/cm2. (See for example, Hoffmann, K.; Mix, R.; Friedrich, J. F.; Resch-Genger, U. In *Reviews in Fluorescence* 2008; Geddes, C. D., Ed.; Springer New York: New York, N.Y., 2010; pp. 139-160 and Ivanov, V.; Behnisch, J.; Hollander, A.; Mehdorn, F.; Zimmermann, H. Surf Interface Anal 1996, 24, 257-262).

The ability to track nanoparticles is critical for investigating the potential of the particles to migrate and/or transfer from polymer matrices into biological systems and the environment. A preliminary migration test is carried out to assess the ability to track the rhodamine and fluorescein-labeled o-MMT from the polymer matrix of a nanocomposite film into a solvent, and the rhodamine is reported. Using a migration cell (ASTM D4754), the rhodamine-labeled nanocomposite films are thoroughly rinsed with aqueous ethanol solution before the migration study were exposed to ethanol at 80° C. for 4 hours. Ethanol is widely used as a food simulant to simulate alcoholic drink and fatty-food systems as recommended by the Food and Drug Administration. (See for example, FDA (U.S. Food and Drug Administration) *Guidance for Industry: Preparation of Premarket Submissions for Food Contact Substances: Chemistry Recommendations*).

A temperature of 80° C. is chosen to simulate accelerate conditions and hot filling operation that these materials could be exposed to. After exposure, the ethanol is placed in a cuvette and allowed to evaporate to isolate any migrated precipitate for CLSM analysis.

Figure 10C:
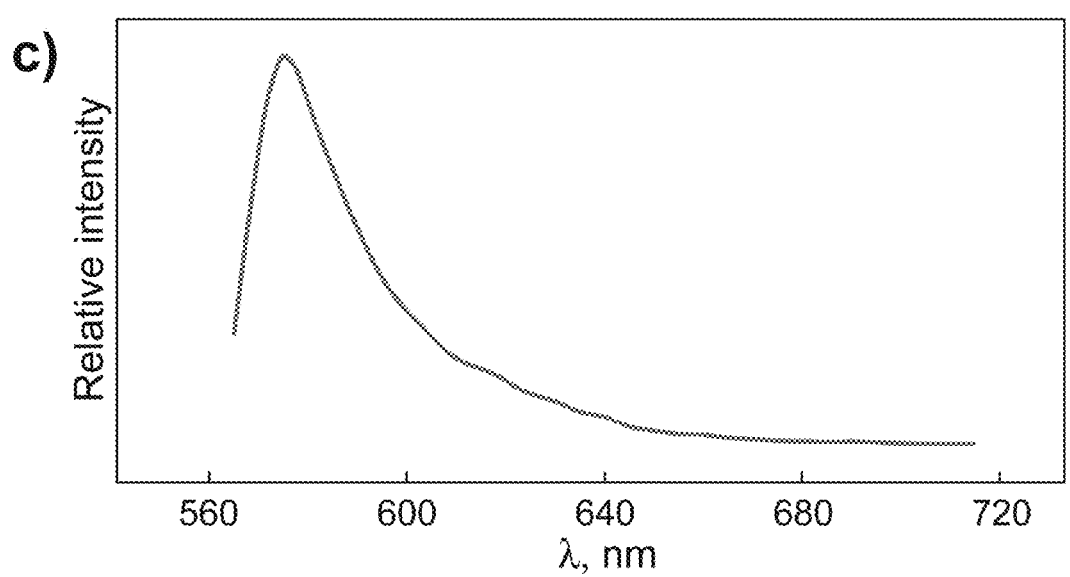
FIG. 10c is a graph illustrating fluorescence emission spectra including excitation wavelengths of the fluorescent-labeled nanoclay particles included in the residue contained in the cuvette after the migration test shown in FIG. 10b, according to an embodiment of the present invention.

FIG. 10a is an image of cuvettes including solvents used during a migration test. FIG. 10b are confocal micrograph image of residue in the cuvette shown in FIG. 10a after the migration test including fluorescent-labeled nanoclay particles. FIG. 10c is a graph illustrating fluorescence emission spectra including excitation wavelengths of the fluorescent-labeled nanoclay particles included in the residue contained in the cuvette after the migration test shown in FIG. 10b. FIG. 10a compares sample cuvettes after evaporation of the solvent taken from the migration cell before the exposure test (shown in FIG. 10a, left) and after the test (shown in FIG. 10a, right). In the illustrated embodiment, residue is observed only in the latter cuvette (shown in FIGS. 10a and 10b) and is attributed to nanocomposite components that migrated into the solvent. Confocal microscopy of the residue (shown in FIG. 10b) shows well defined bright particles, which confirms the migration of labeled o-MMT into the solvent. In addition, the emission spectrum of the particles (shown in FIG. 10c) matched the characteristic spectrum from the rhodamine-labeled clay (shown in FIG. 9c). These results demonstrate the ability of the methodology to track labeled o-MMT movement from one medium to another (from the nanocomposite into the simulant or solvent). Additionally, work is being pursued to evaluate the free surface energy and the surface properties of the labeled-nanoclays, and to determine if the modification on the clay due to the presence of the label has an impact on the diffusion pattern of nanoclays.

In summary, a new method for the fluorescent labeling of nanoclays is developed that covalently attaches fluorescein-5-maleimide (fluorescein) or tetramethylrhodamine-5-maleimide (rhodamine) to silane-treated o-MMT. The tagging is confirmed via CLSM. Both fluorescent labels show good thermal stability up to 220° C. and the rhodamine label withstood 250° C. After the labeled o-MMT is incorporated into a polypropylene matrix and nanocomposite films are extruded, the fluorescent labels are again detected with CLSM. Preliminary migration testing with rhodamine-labeled o-MMT shows that some nanoclay migrated from the polymer matrix into the solvent (i.e., ethanol). The proposed methodology has the potential to track o-MMT and other nanoclays in various polymer nanocomposite systems and detect nanoparticle migration into solvents or possibly other surrounding environments like biological systems.

EXAMPLE 2

In one embodiment, the method of detecting a migration of nanoclay particles from a nanocomposite film to a solvent, according to the present invention, includes (S1) labeling the nanoclay, (S2) detecting and characterize fluorescence from labeled nanoclay, (S3) determining the thermal stability of the labeled nanoclay, (S4) incorporating the labeled nanoclay in the polymer matrix, and (S5) tracking labeled nanoclay that migrated from the polymer matrix into a solvent.

S1. Labeling of Nanoclay.
Materials

In the illustrated embodiment, nanoclay (Nanomer® I.44P), containing 35-45% quaternary ammonium compounds, bis(hydrogenated tallow alkyl)dimethyl, chlorides; 55-65% montmorillonite (MMT) is selected. Linear polypropylene (PP, Profax 6523) is used as the model matrix and maleic anhydride-grafted-PP (MA-g-PP or MAPP, Bondyram® 1001, 1 wt % bound maleic anhydride) is used as the compatibilizer. Silane (3-mercaptopropyl)-trimethoxysilane (>95%) is used to functionalize the nanoclays. Two fluorescent dyes, tetramethylrhodamine-5-maleimide (rhodamine) and fluorescein-5-maleimide (fluorescein) are used for tagging.

For example, the properties of the fluorescent dyes including the properties of fluorescent probes as reported by Molecular Probes may be provided as in the following chart.

|  | tetramethylrhodamine-5-maleimide | fluorescein-5-maleimide |
| --- | --- | --- |
| Molecular formula | $C_{28}H_{23}N_3O_5$ | $C_{24}H_{13}NO_7$ |
| Molecular weight | 481.51 | 427.37 |
| Absorption maximum, nm | 541 | 592 |
| Emission maximum, nm | 567 | 515 |

Thiol reactive dyes are selected for selective reaction with the functionalized nanoclay.
Methods
Silyation.

In the illustrated embodiment, for silyation, a mercaptosilane are selected for the functionalization of the nanoclay. The silyation treatment is carried out using following the procedure of Chaudhary. See for example, Chaudhary, A. K. Rheology modification and foaming of polypropylene—clay nanocomposites with coupling agents, Ph. D. Dissertation. Michigan State University, 2010. Organomodified montmorillonite (o-MMT) (15 g) is dispersed in 500 mL of a solvent (80 wt % methanol+20 wt % deionized water) using a magnetic stirrer. In a separate flask, 4.5 g of silane is diluted with 200 mL of the same solvent. This diluted silane solution is slowly added to the clay dispersion and stirred for 6 h at 23° C. The clay suspension is filtered and washed at least 3 times using the original solvent to remove any unreacted silane. The resulting clay cake is dried for 24 hours under vacuum at 80° C., 20" Hg pressure ($6.8 \times 10^{-4}$ Pa, abs). The cured clay is then powdered using a mortar and pestle and shaken through a No. 200 (75 µm) sieve.

Conjugation.

In the illustrated embodiment, the conjugation procedure for both fluorescent labels is carried out in a phosphate buffered saline (PBS) solution: 10 mg of the fluorescent dye was dissolved in 240 mL PBS. The fluorescein-based dye is dissolved directly in PBS, whereas the rhodamine-based dye is first dissolved in methanol (10 mL) and then the stock solution is dissolved in PBS. Modified nanoclay (treated with mercaptosilane, 0.25 g) is dissolved in 100 mL ethanol and carefully added to the PBS solution containing the dye. The solution is shaken and stirred with a magnetic stirrer for 1 hour (incubation time). The clay is separated from the solution by centrifuging the mixture at 2500 rpm for 5 min. To remove unreacted dye, the clay pellets are washed in ethanol and centrifuged; this washing cycle is repeated at least 3 times or until a clear solution is obtained.

S2. Fluorescence Characterization

In the illustrated embodiment, fluorescence detection and characterization of emission spectra is done via confocal laser scanning microscopy (CLSM). The images are acquired using an Olympus FluoView FV1000 CLSM configured on a fully automated inverted IX81 microscope. For rhodamine, the fluorescence is excited using the 543 nm line of the Helium Neon laser and the fluorescence signal in red emission is captured using a 560 long pass filter. For fluorescein, the fluorescence is excited using the 488 nm line of the Argon laser and the green emission is captured using a 505-525 nm band pass filter. The transmitted light image are generated in a brightfield mode. To record the emission spectra from the rhodamine-labeled nanoclay samples, excitation is provided by the 559 nm solid state diode laser, with the emission recorded from 565-720 nm in 5-nm increments. The fluorescein-labeled nanoclay is excited at 488 nm and the emission spectra recorded from 500-740 nm in 10-nm increments.

In the illustrated embodiment, Olympus FluoView FV1000 Advanced Software is used to analyze each emission spectrum. Regions of interest are traced around particles, and the average fluorescence intensity of each region is calculated and plotted for each wavelength.

In addition, confocal microscopy-aided autofluorescence characterization (spectrophotometric analysis) of the unlabeled clay is carried out. Autofluorescence characterization can assist in the selection of a fluorescent dye by providing information of scattered emissions that can interfere with the fluorescent tag. In one embodiment, at the excitation wavelengths from 405 nm to 488 nm, the unlabeled clay emission peak at 500 nm, which overlapped with the fluorescein-tagged clay (emission peak at 515 nm when excited at 488 nm). However, there is no interference with the rhodamine-tagged clay, which usually excites at a wavelength of 543 nm and has an emission peak at 567 nm beyond the autofluorescence of the unlabeled clay. Depending on the different components in the nanocomposite that may produce autofluorescence, one can select which dye to use.

Thermal Stability Test.

In the illustrated embodiment, thermal stability tests are performed using a thermogravimetric analysis (TGA) instrument (TA Instruments model Q50). Labeled nanoclay (2 to 5 mg) are placed in an aluminum pan and heated to the desired temperature (i.e., 220° C. or 250° C.) and held at that temperature for 15 min. A continuous purge of nitrogen (60 mL/min) is maintained during the experiment. After heating, the samples are mounted on a glass microscope slide for confocal analysis.

Multiple emission spectra are recorded for each sample and the relative integral fluorescence emission (RIFE) was calculated such that:

$$RIFE = I_t/I_o \qquad \text{Eq. S1}$$

where $I_t$ is the integral of fluorescent intensity vs. wavelength for each emission spectra, and $I_o$ is the integral for the average intensity of the unheated sample.

Incorporation of Labeled Nanoclays Into a Polymer Matrix.

In the illustrated embodiment, the polypropylene is blended with about 3 wt % nanoclay and about 12 wt % compatibilizer (maleic anhydride modified polypropylene) to enhance dispersion of the nanoclay. Labeled and unlabeled nanocomposites are prepared. The labeled nanocomposites include about 15 wt % of either fluorescent-labeled clay based on the total amount of clay (3 wt %). The mixing is performed with an internal mixer (CW Brabender, Duisburg, Germany) heated at 180° C. for 6 min at 80 rpm under a nitrogen atmosphere. The melt-mixed batch is used to produce films of around 100 μm in thickness, prepared via compression molding (175° C., 10 tons) using a Teflon mold.

Figure 11B:
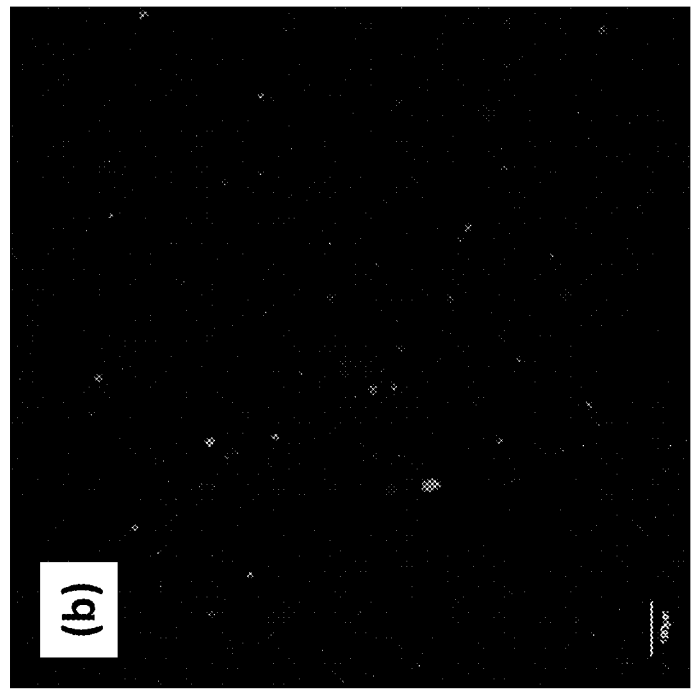
FIG. 11b is a confocal micrograph image of a nanocomposite film including rhodamine-labeled nanoclay particles, according to an embodiment of the present invention.
Figure 11A:
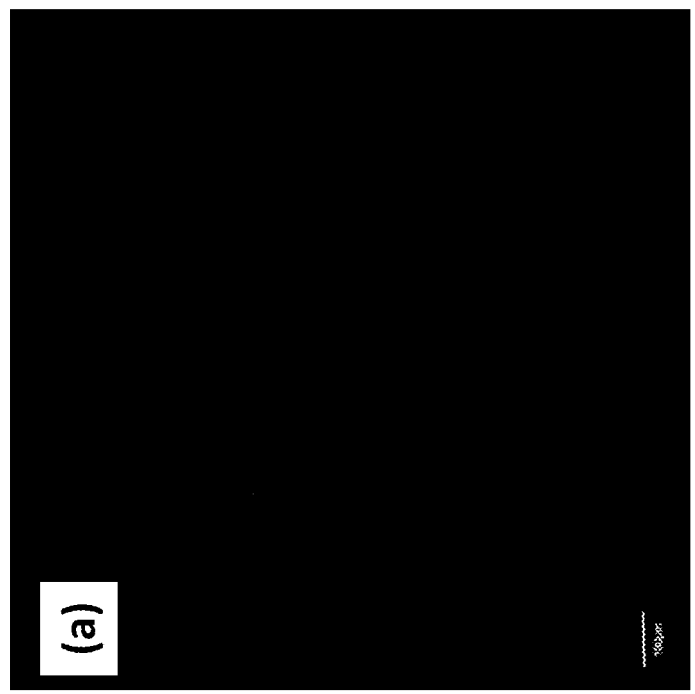
FIG. 11a is a confocal micrograph image of a control nanocomposite film without fluorescent-labeled nanoclay particles, according to an embodiment of the present invention.
Figure 12B:
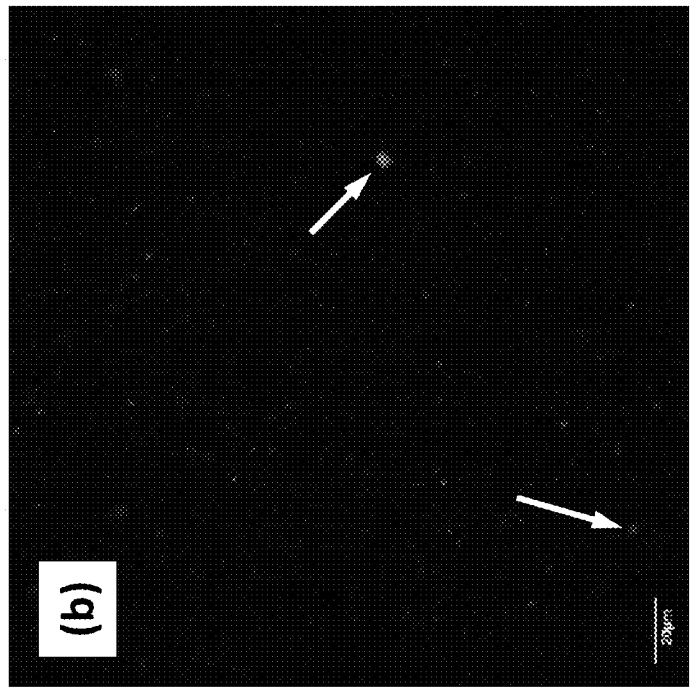
FIG. 12b is a confocal micrograph image of a nanocomposite film including fluorescein-labeled nanoclay particles, according to an embodiment of the present invention.
Figure 12A:
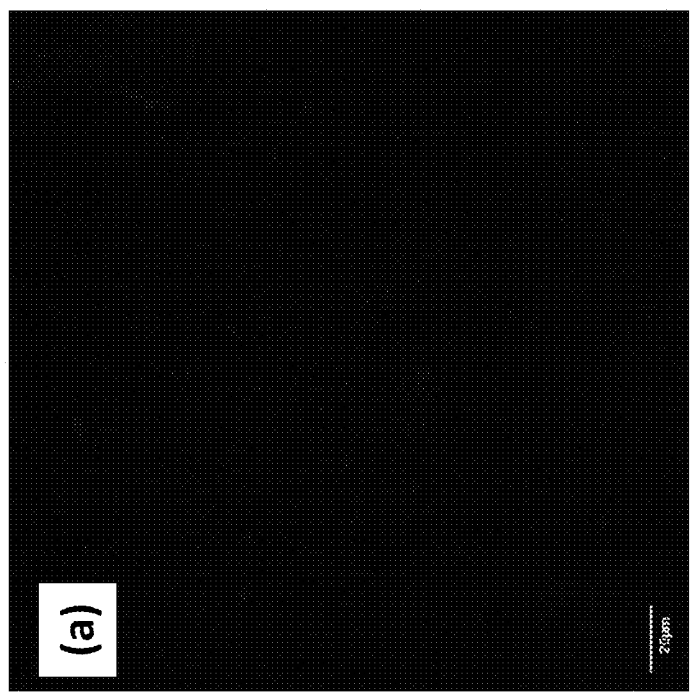
FIG. 12a is a confocal micrograph image of a control nanocomposite film without fluorescent-labeled nanoclay particles, according to an embodiment of the present invention.

FIG. 11a is a confocal micrograph image of a control nanocomposite film without fluorescent-labeled nanoclay particles. FIG. 11b is a confocal micrograph image of a nanocomposite film including rhodamine-labeled nanoclay particles. FIG. 12a is a confocal micrograph image of a control nanocomposite film without fluorescent-labeled nanoclay particles. FIG. 12b is a confocal micrograph image of a nanocomposite film including fluorescein-labeled nanoclay particles. The contrast between the fluorescent-labeled and the unlabeled nanocomposite films when analyzed by CLSM at the same conditions is shown in FIGS. 11a and 11b for rhodamine and in FIGS. 12a and 12b for fluorescein.

Tracking of labeled nanoclay from the polymer matrix into a solvent.

FIG. 13a is a confocal micrograph image of migrated residue from nanocomposite film without fluorescent-labeled nanoclay particles. FIG. 13b is a confocal micrograph image of migrated reside from nanocomposite film including rhodamine-labeled nanoclay particles. In the illustrated embodiment, in addition to the migration results described herein a two-sided migration test is performed following ASTM D4754, where PP-clay nanocomposite films with and without rhodamine-labeled nanoclay are exposed to ethanol. PP-clay nanocomposites are thoroughly rinsed with aqueous ethanol solution before the migration study. Using a temperature bath set at 80° C., the samples are exposed to the solvent at the elevated temperature for 4 hours. The solvent is collected before and after the 4-hour migration period, placed in cuvettes and allowed to evaporate inside a fume hood. The residue left in the cuvette is analyzed through CLSM.

The above-described engineered nanomaterials and methods overcome at least some disadvantages of known engineered nanomaterials by providing a nanoclay particle having a fluorescent probe to facilitate monitoring a movement of the nanoclay particle with respect to a material. More specifically, the nanoclay particle includes a fluorescent tag that is covalently bonded to the nanoclay particle to provide stability to the bond between the fluorescent tag and the nanoclay particle. The fluorescent tag is adapted to emit fluorescence signals that may be detected using laser scanning microscopy to facilitate determining a location of the nanoclay particle. In addition, the nanoclay particle is adapted to be attached to a material to facilitate monitoring a location of the nanoclay particle within the material and monitor a migration of the nanoclay particle from the material and into a surrounding environment. By providing a nanoclay particle that includes a including a fluorescent probe, the movement and position of a single and/or a cluster of nanoclay particles may be tracked to evaluate the transport of ENMs from nanocomposites and/or biological systems.

Exemplary embodiments of methods of monitoring a position of a nanoclay particle in nanocomposite materials are described above in detail. The methods are not limited to the specific embodiments described herein, but rather, steps of the method may be utilized independently and separately from other steps described herein. For example, the method may also be used in combination with other methods for detecting nanoparticles, and is not limited to practice with only the nanoclay particles and the nanocomposite material as described herein. Rather, an exemplary embodiment can be implemented and utilized in connection with many other nanoparticle monitoring applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Other aspect and features of the present invention can be obtained from a study of the drawings, the disclosure, and the appended claims. The invention may be practiced otherwise than as specifically described within the scope of the appended claims. It should also be noted, that the steps and/or functions listed within the appended claims, notwithstanding the order of which steps and/or functions are listed therein, are not limited to any specific order of operation.

Although specific features of various embodiments of the invention may be shown in some drawings and not in others, this is for convenience only. In accordance with the principles of the invention, any feature of a drawing may be referenced and/or claimed in combination with any feature of any other drawing.

What is claimed is:

1. A nanoparticle prepared by a process comprising the steps of:
   providing a nanoclay particle including organically modified montmorillonite (o-MMT);
   reacting the nanoclay particle with a solution including mercaptosilane to convert a hydroxyl of the o-MMT to a thiol moiety and produce a mercaptosilane modified nanoclay particle; and
   reacting the mercaptosilane modified nanoclay particle with a thiol-reactive dye, the thiol-reactive dye including a fluorescent tag, to attach the fluorescent tag to the thiol moiety of the mercaptosilane modified nanoclay particle with a covalent bond to form a fluorescent-labeled nanoclay particle.

2. A nanoparticle in accordance with claim 1, wherein the fluorescent tag is selected from a group consisting of fluorescein and rhodamine.

3. A nanoparticle in accordance with claim 1, wherein the step of reacting the nanoclay particle with a solution including mercaptosilane further includes the steps of:
   dispersing the nanoclay particle in an aqueous solution to form a clay dispersion; and
   mixing the solution including mercaptosilane with the clay dispersion to facilitate reacting the nanoclay particle with the mercaptosilane to form the mercaptosilane modified nanoclay particle.

4. A nanocomposite film prepared by a process comprising the steps of:
   providing a polypropylene matrix material;
   providing a plurality of nanoclay particles including organically modified montmorillonite (o-MMT);
   reacting the plurality of nanoclay particles with a solution including mercaptosilane to convert a hydroxyl of the o-MMT to a thiol moiety and producing a plurality of mercaptosilane modified nanoclay particles;
   reacting the plurality of mercaptosilane modified nanoclay particles with a thiol-reactive dye, the thiol-reactive dye including at least one fluorescent tag, to attach the fluorescent tag to the thiol moiety of at least one mercaptosilane modified nanoclay particle of the plurality of mercaptosilane modified nanoclay particles to form a fluorescent-labeled nanoclay particle;
   attaching the fluorescent-labeled nanoclay particle to the polypropylene matrix material; and
   extruding the mixture to form a nanocomposite material.

5. A nanocomposite film in accordance with claim 4, wherein the fluorescent tag is selected from a group consisting of fluorescein and rhodamine.

6. A method of forming a nanoclay particle, including the steps of:
   providing a nanoclay particle including organically modified montmorillonite (o-MMT);
   reacting the nanoclay particle with a solution including mercaptosilane to convert a hydroxyl of the o-MMT to a thiol moiety to form a modified mercaptosilane modified nanoclay particle including thiol moieties; and
   reacting the mercaptosilane modified nanoclay particle with a thiol-reactive dye to form a fluorescent-labeled nanoclay particle.

7. A method in accordance with claim 6, wherein the thiol-reactive dye includes a fluorescence probe.

8. A method in accordance with claim 7, wherein the fluorescence probe is selected from a group consisting of fluorescein and rhodamine.

9. A method in accordance with claim 7, wherein the fluorescence probe is attached to the nanoclay particle with a covalent bond.

10. A method in accordance with claim 6, wherein the step of reacting the nanoclay particle with a solution including mercaptosilane further including the steps of:
    dispersing the nanoclay particle in an aqueous solution to form a clay dispersion; and
    mixing the solution including mercaptosilane with the clay dispersion to facilitate reacting the nanoclay particle with the mercaptosilane to form the mercaptosilane modified nanoclay particle.

11. A method in accordance with claim 10, wherein the aqueous solution includes methanol and deionized water.

12. A method in accordance with claim 10, further including the steps of:
    filtering and washing the clay suspension to remove unreacted mercaptosilane; and
    curing the clay suspension to form a clay cake including the modified nanoclay particle.

13. A method in accordance with claim 12, further including the steps of:
    dissolving a fluorescence probe in a saline solution;
    dissolving the clay cake in an alcohol solution;
    mixing the saline solution and the alcohol solution to facilitate reacting the fluorescence probe with the modified nanoclay particle to form the fluorescent-labeled nanoclay particle; and
    separating the fluorescent-labeled nanoclay particle from the mixed solution with centrifuging.

14. A method in accordance with claim 13, wherein the saline solution includes a phosphate buffered saline solution.

* * * * *

UNITED STATES PATENT AND TRADEMARK OFFICE
CERTIFICATE OF CORRECTION

PATENT NO. : 9,890,325 B2
APPLICATION NO. : 15/230128
DATED : February 13, 2018
INVENTOR(S) : Maria I. Rubino Page 1 of 1

It is certified that error appears in the above-identified patent and that said Letters Patent is hereby corrected as shown below:

In the Claims

Column 16, Line (30): Claim 1 Please delete "and" and replace with --and,--

Column 16, Line (66): Claim 4 Please delete "and" and replace with --and,--

Signed and Sealed this
Twenty-seventh Day of March, 2018

Andrei Iancu
*Director of the United States Patent and Trademark Office*